(12) United States Patent
Abdelmoaty et al.

(10) Patent No.: US 11,464,618 B2
(45) Date of Patent: Oct. 11, 2022

(54) INTESTINAL LENGTHENING DEVICE

(71) Applicant: Providence Health & Services—Oregon, Portland, OR (US)

(72) Inventors: Walaa F. Abdelmoaty, Portland, OR (US); Lee L. Swanstrom, Portland, OR (US); Christy M. Dunst, Portland, OR (US); Frédéric Mouret, Castelnau le Lez (FR); David Baas, Strasbourg (FR)

(73) Assignee: Providence Health & Services—Oregon, Portland, OR (US)

( * ) Notice: Subject to any disclaimer, the term of this patent is extended or adjusted under 35 U.S.C. 154(b) by 32 days.

(21) Appl. No.: 16/636,607

(22) PCT Filed: Aug. 7, 2018

(86) PCT No.: PCT/US2018/045570
§ 371 (c)(1),
(2) Date: Feb. 4, 2020

(87) PCT Pub. No.: WO2019/032560
PCT Pub. Date: Feb. 14, 2019

(65) Prior Publication Data
US 2020/0368007 A1 Nov. 26, 2020

Related U.S. Application Data

(60) Provisional application No. 62/542,186, filed on Aug. 7, 2017.

(51) Int. Cl.
*A61F 2/04* (2013.01)
*A61B 34/00* (2016.01)
*A61B 90/00* (2016.01)

(52) U.S. Cl.
CPC ............... *A61F 2/04* (2013.01); *A61B 34/73* (2016.02); *A61B 90/02* (2016.02);
(Continued)

(58) Field of Classification Search
CPC combination set(s) only.
See application file for complete search history.

(56) References Cited

U.S. PATENT DOCUMENTS

| 7,722,560 B2 | 5/2010 | Teitelbaum et al. |
| 9,138,336 B2 | 9/2015 | Carman et al. |

(Continued)

OTHER PUBLICATIONS

"American Gastroenterological Association Medical Position Statement: Short Bowel Syndrome and Intestinal Transplantation," vol. 124, No. 4, 2003 (pp. 1105-1110).

(Continued)

*Primary Examiner* — Yashita Sharma
(74) *Attorney, Agent, or Firm* — Klarquist Sparkman, LLP

(57) ABSTRACT

An implantable distraction device includes a tubular member oriented along a longitudinal axis, and curved first and second attachment members coupled to the tubular member and configured to be sutured within a body lumen. The second attachment member is spaced apart from the first attachment member along the tubular member. The device further includes at least one magnet coupled to the tubular member and movable relative to the tubular member. At least one of the first attachment member or the second attachment member is axially movable relative to the other to vary an axial distance between the first and second attachment members. The at least one magnet is configured such that motion of a magnetic field relative to the distraction device causes corresponding motion of the at least one magnet, and corresponding motion of one attachment member relative to the other.

22 Claims, 20 Drawing Sheets

(52) U.S. Cl.
CPC ... *A61B 2034/731* (2016.02); *A61F 2002/045* (2013.01); *A61F 2210/009* (2013.01); *A61F 2250/0007* (2013.01)

(56) References Cited

U.S. PATENT DOCUMENTS

| | | | | |
|---|---|---|---|---|
| 2002/0032484 | A1* | 3/2002 | Hyde, Jr. | A61N 2/06 623/18.12 |
| 2006/0004459 | A1* | 1/2006 | Hazebrouck | A61F 2/36 623/23.45 |
| 2007/0276378 | A1 | 11/2007 | Harrison et al. | |
| 2009/0240339 | A1 | 9/2009 | Teitelbaum et al. | |
| 2011/0087252 | A1 | 4/2011 | Chmura | |
| 2011/0238126 | A1* | 9/2011 | Soubeiran | A61B 17/7216 606/86 R |
| 2015/0313745 | A1* | 11/2015 | Cheng | A61F 5/028 602/19 |

OTHER PUBLICATIONS

Chawla and Teitelbaum, "Profound systemic inflammatory response syndrome following non-emergent intestinal surgery in children," *J Pediatr Surg.*, vol. 48, No. 9, Sep. 2013 (pp. 1936-1940).

Demehri et al., "Development of an Endoluminal Intestinal Lengthening Device Using a Geometric Intestinal Attachment Approach," *Surgery*, vol. 158, No. 3, Sep. 2015 (pp. 802-811).

International Search Report and Written Opinion issued in corresponding PCT Application No. PCT/US2018/045570, dated Nov. 29, 2018 (9pps).

Koga et al., "Distraction-induced intestinal enterogenesis: Preservation of intestinal enterogenesis: Preservation of intestinal function and lengthening after re-implantation into normal jejunum," *Ann Surg*, vol. 255, No. 2, Feb. 2012 (pp. 302-310).

Okawada, et al., Distraction induced Entergogenesis: A unique mouse model using polyethylene glycol, *J Surg Res*, vol. 170, No. 1, Sep. 2011 (pp. 41-47).

Ralls et al., "Mesenteric Neovascularization with Distraction-Induced Intestinal Growth: Enterogenesis," *Pediatr Surg Int.*, vol. 29, No. 1, Jan. 2013 (pp. 33-39).

Rouch and Dunn, "New insights and interventions for short bowel syndrome," *Curr Pediatr Rep.*, vol. 5, No. 1, Mar. 2017 (pp. 1-5).

Safford et al., "Longitudinal mechanical tension induces growth in the small bowel of juvenile rats," *Gut*, vol. 54, 2005 (pp. 1085-1090).

Spencer et al., "Enterogenesis in a clinically feasible model of mechanical small-bowel lengthening," *Surgery*, vol. 140, No. 2, Aug. 2006 (pp. 212-220).

Spencer et al., "Pediatric short-bowel syndrome: the cost of comprehensive care," American Society for Nutrition, vol. 88, 2008 (pp. 1552-1559).

Spencer et al., "Pediatric Short Bowel Syndrome: Redefining Predictors of Success," *Annals of Surgery*, vol. 242, No. 3, Sep. 2005 (pp. 403-412).

Stark et al., "Development of an endoluminal intestinal lengthening capsule," *Journal of Pediatric Surgery*, vol. 47, 2012 (pp. 136-141).

Sueyoshi et all, "Glucagon-Like Peptide 2 Increases Efficacy of Distraction Enterogenesis," *J Surg Res.*, vol. 184, No. 1, Sep. 2013 (pp. 365-373).

Warner, "Tissue Engineered Small Intestine: A Viable Clinical Option?" *Lippincott Williams & Wilkins*, 2004 (pp. 775-756).

Winkler and Smith, "Clinical, Social, and Economic Impacts of Home Parenteral Nutrition Dependence in Short Bowel Syndrome," *Journal of Parenteral and Enteral Nutrition*, vol. 38, Supp. 1, May 2014 (pp. 32S-37S).

Al-Mahdi, "Clinical Evaluation of Distraction Osteogenesis in the Treatment of Mandibular Hypoplasia," *J of Craniofacial Surgery*, vol. 24, No. 1, Jan. 2013 (pp. e50-e57).

Banerjee & Warwicker, "Acute renal failure and metabolic disturbances in the short bowel syndrome," *Q J Med*, vol. 95, 2002 (pp. 37-40).

Bezwada et al., "Monocryl suture, a new ultra-pliable absorbable monofilament sutures," *Biomaterials*, No. 16, No. 15, 1995 (pp. 1141-1148).

Buchman, "The Medical and Surgical Management of Short Bowel Syndrome," *MedGenMed*, vol. 6, No. 2, 2004 (10pps.).

Cavicchi et al., "Prevalence of Liver Disease and Contributing Factors in Patients Receiving Home Parenteral Nutrition for Permanent Intestinal Failure," *Annals of Internal Medicine*, vol. 132, No. 7, Apr. 4, 2000 (pp. 525-532).

Ching et al., "Pediatric intestinal failure: nutrition, pharmacologic, and surgical approaches," *Nutr Clin Pract*, vol. 22, No. 6, 2007 (pp. 653-663).

Diamond et al., "Neonatal short bowel syndrome outcomes after the establishment of the first Canadian multidisciplinary intestinal rehabilitation program: preliminary experience," *J Pediatr Surg*, vol. 42, 2007 (pp. 806-811).

DiBaise et al., "Intestinal rehabilitation and the short bowel syndrome: part 1," *Am J Gastroenterol*, vol. 99, 2004 (pp. 1386-1395).

Dionigi et al., "Extraluminal helicoidal stretch (Helixtretch): A novel intestinal lengthening," *J Pediatr Surg*, vol. 49, 2014 (pp. 1787-1790).

Eriksen et al., "A prospective randomized study comparing two different expander approaches in implant-based breast reconstruction: one stage versus two stages," *Plast Reconstr Surg*, vol. 130, No. 2, 2012 (pp. 254e-264e).

Frongia et al., "Comparison of LIFT and STEP procedures in children with short bowel syndrome—A systematic review of the literature," *Pediatr Surg*, vol. 48, 2003 (pp. 1794-1805).

Galea et al., "Short-Bowel Syndrome: A Collective Review," *J Pediatr Surg*, vol. 27, No. 5, May 1992 (pp. 592-596).

Goulet & Sauvat, "Short bowel syndrome and intestinal transplantation in children," *Curr Opin Clin Nutr Metab Care*, vol. 9, No. 3, 2006 (pp. 304-313).

Grant, "Intestinal Transplantation: 1997 Report of the International Registry," *Wolters Kluwer Health, Inc.*, vol. 67, No. 7, Apr. 15, 1999 (pp. 1061-1064).

Kim et al., "A novel treatment for the midaortic syndrome," *N Engl J Med*, vol. 367, No. 24 (pp. 2361-2362).

Kurkchubasche et al., "Adaptation in short bowel syndrome: reassessing old limits," *J Pediatr Surg*, No. 28, 1993 (pp. 1069-1071).

Liu et al., "Chronic urogenital sinus expansion in reconstruction of high persistent cloaca," *Pediatr Surg Int*, vol. 28, Jul. 21, 2012 (pp. 835-840).

Mahour et al., "Elongation of the Upper Pouch and Delayed Anatomic Reconstruction in Esophageal Atresia," *J of Pedatr Surg*, vol. 9, No. 3, Jun. 1974 (pp. 373-383).

Park et al., "Enterogenesis by Mechanical Lengthening: Morphology and Function of the Lengthened Small Intestine," *J of Pediatr Surg*, vol. 39, No. 12, Dec. 2004 (pp. 1823-1827).

Sudan, "Long-term outcomes and quality of life after intestine transplantation," *Lippincott Williams & Wilkins, Inc.* vol. 15, No. 3, Jun. 1010 (pp. 357-360).

Sullins et al., "Function of mechanically lengthened jejunum after restoration into continuity," *J Pediatr Surg*, vol. 49, No. 6, (pp. 971-974).

Sullins et al., "A novel biodegradable device for intestinal lengthening," *J Pediatr Surg*, vol. 49, 2014 (pp. 109-113).

Wales & Christison-Lagay, "Short bowel syndrome: epidemiology and etiology," *Seminars in Pediatr Surg*, vol. 19, 2010 (pp. 3-9).

Wales et al., "Neonatal short bowel syndrome: population-based estimates of incidence and mortality rates," *J Pediatr Surg*, vol. 39, No. 5, May 2004 (pp. 690-695).

Weih et al., "Current practice and future perspectives in the treatment of short bowel syndrome in children—a systemic review," *Langenbecks Arch Surg*, vol. 397, 2012 (pp. 1043-1051).

\* cited by examiner

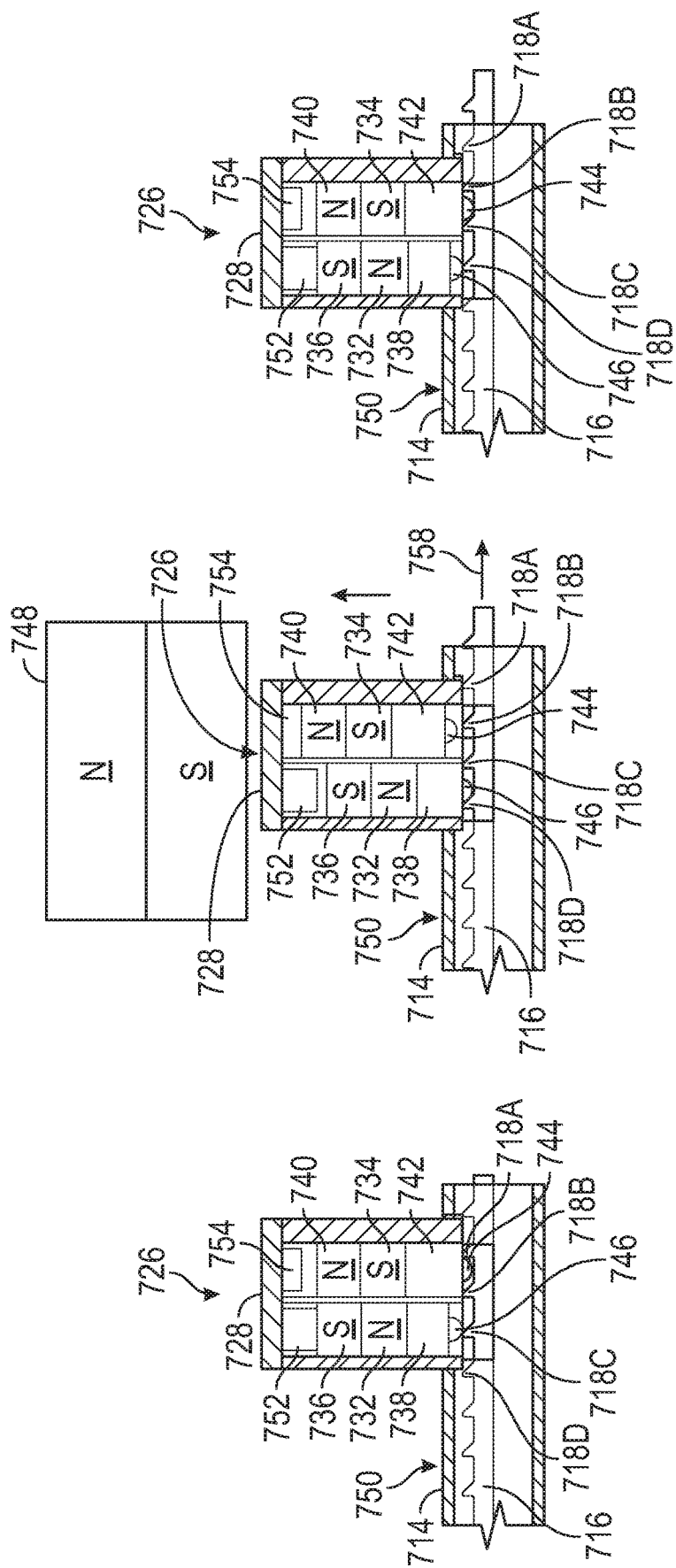

INTESTINAL LENGTHENING DEVICE

CROSS REFERENCE TO RELATED APPLICATION

This is the U.S. National Stage of International Application No. PCT/US2018/045570, filed Aug. 7, 2018, which was published in English under PCT Article 21(2), which in turn claims the benefit of U.S. Provisional Application No. 62/542,186, filed Aug. 7, 2017. The disclosures of International Application No. PCT/US2018/045570 and U.S. Provisional Application No. 62/542,186 are incorporated herein by reference in their entirety.

FIELD

The present application relates to devices and methods for lengthening lumens or organs of the body.

BACKGROUND

Short bowel syndrome (SBS) is a complex malabsorptive disease that results from physical loss of large parts of the small intestine or loss of the function. (Galea et al., Short bowel syndrome: a collective review. *J Pediatr Surg* 1992: 27:592-6). Patients with SBS have insufficient absorptive capacity to provide an adequate alimentary supply. (Weih et al., Current practice and future perspectives in the treatment of short bowel syndrome in children—a systemic review. *Langenbecks Arch Surg* 2012:397:1043-51). It may be also defined as the need for prolonged parenteral nutrition (PN) secondary to intestinal failure after bowel resection. (Kurkchubasche et al., Adaptation in short bowel syndrome: reassessing old limits. *J Pediatr Surg* 1993:28:1069-71). Intestinal failure (IF) refers to a malabsorptive state in which the residual intestinal function is inadequate to support growth, nutrition and hydration. SBS is a common cause of IF in pediatrics. (Wales et al., Short bowel syndrome: epidemiology and etiology. *Seminars in Pediatr Surg* 2010: 19:3-9). In some cases, SBS exists when a patient's residual intestinal function is inadequate to sustain survival, growth, hydration, and electrolyte homeostasis. (Weih et al., Current practice and future perspectives in the treatment of short bowel syndrome in children—a systemic review. *Langenbecks Arch Surg* 2012:397:1043-51).

SBS can be caused by extensive resection of the small intestine due to a number of different reasons. Necrotizing enterocolitis (NEC) is the most common cause of neonatal SBS and accounts for at least 30% of most reported cases, whereas volvulus and trauma are the leading causes in the non-neonatal population. In older children and adults, the long-segment resections for Crohn's disease, ischemic vascular disease, radiation enteritis, malignancy, trauma, and adhesive obstructions are common causes.

Accurate estimation of SBS incidence is difficult due to discrepancies in SBS definition among studies, lack of follow-up data, and inability of large centers to define their studies population as a result of complex referral patterns. However, Wales et al. demonstrated that the neonatal SBS incidence was found to be 24.5 per 100,000 live births (95% confidence interval (CI) 12.1, 36.9) in a population-based study, which examined SBS incidence and mortality using the administrative healthcare data and federal census data. (Wales et al., Neonatal short bowel syndrome: population-based estimates of incidence and mortality rates. *J Pediatr Surg.* 2004:39:690-5). There is a much higher incidence of SBS in preterm (less than 37-week gestation) compared with term newborns (353.7/100,000 live births vs 3.5/100,000 live births). The most common causes among the preterm group were NEC (35%), complicated meconium ileus (20%), abdominal wall defects (12.5%), intestinal atresia (10%), and volvulus (10%). However, the number of infant SBS cases due to NEC is expected to increase as more extremely premature infants are resuscitated and survive the initial weeks after birth. Also, the increase in the survival rate of infants with complex congenital heart disease will increase the number of patients with SBS due to ischemic intestinal complications.

Mortality rates vary tremendously or are not reported at all. There is a possibility that SBS survival in published reports are overestimated due to a selection bias, as early deaths are often excluded. (Wales P W, Christison-Lagay E R. Short bowel syndrome: epidemiology and etiology. Seminars in Pediatr Surg 2010:19:3-9). In the Wales et al. study the mortality rate was found to be 37.5% with 60% of SBS-related deaths were because of hepatic failure. Other studies reported similar mortality rates of 20%-40%, which have remained relatively constant during the past several decades, despite advances in neonatal care. (Spencer et al., Pediateric short bowel syndrome: the cost of comprehensive care. *Am J Clin Nutr* 2008:88:1552-9).

Despite the improvement of medical and surgical methods to treat SBS, the morbidity and mortality remain considerably high. Medical management of SBS aims to maintain fluid, electrolyte, and nutrient balances. As SBS is mainly a malabsorptive disorder, nutrition must be provided parenterally (PN), at least partially. Many complications are associated with PN, such as central line complications, multiple systemic infections, cholestasis, and failure to thrive. But the most serious and potentially fatal complication of PN is liver failure, which occurs in 40%-70% of SBS patients. (Ching et al., Pediatric intestinal failure: nutrition, pharmacologic, and surgical approaches. *Nutr Clin Pract* 2007:22(6):653-63). At this stage, liver and intestinal transplant becomes the only therapeutic option. Unfortunately, most of these patients don't survive to receive a transplant as they are too premature for procedure eligibility. Surgical management available to treat SBS includes small bowel transplantation (SBTx) and intestinal reconstruction procedures. SBTx is reserved for patients with non-functioning bowel remnant, given its challenging postoperative course with potential life threatening complications. The goal of intestinal reconstruction procedures is to lengthen the too short bowel with bowel-lengthening procedures, and to slow down the rapid intestinal transit time with transit-slowing procedures.

Two common lengthening procedures are the longitudinal intestinal lengthening and tailoring (LILT) procedure, and the serial transverse enteroplasty (STEP) procedure. Each procedure has its limitations; however, the LILT procedure can be more technically challenging with lack of adjustability. The STEP procedure can be easier and adjustable, but it alters the physical structure of the intestine, and may contribute to further intestinal failure. None of the procedures has shown to help SBS patients wean off PN in carefully controlled trials. (Rouch et al., New insights and interventions for short bowel syndrome. *Curr Pediatr Rep* 2017:5: 1-5). Furthermore, intestinal lengthening procedures are not for every patient and require specific intestinal length and diameter, and even without any more complications, the rate of weaning of PN is variable. (Weih et al., Current practice and future perspectives in the treatment of short bowel syndrome in children—a systemic review. *Langenbecks Arch Surg* 2012:397:1043-51).

Transit-slowing procedures use different methods such as anti-peristaltic segments, artificial valves, colonic interposition, creating a pouch or loop, or intestinal pacing. These procedures are still in the experimental stage and used only in very few cases, and are associated with a very high morbidity and mortality rates. In general, surgical procedures are highly invasive with serious complications such as intestinal necrosis, perforation, fistulaization, leakage, and abdominal abscesses, and with variable outcomes.

Several factors can affect SBS patients' prognosis, such as the region of the remaining intestinal part, the functional capacity of the residual intestine, the nature of the primary diagnosis and the residual underlying disease, the presence or absence of colon in continuity and the ileocecal valve, and the age of the patient at the time of surgery. However, the most important factor is the residual intestinal length as there is a clear correlation between intestinal length and patient outcome. Buchman demonstrated that the overall survival in SBS patients at 6 years is estimated to be 65% for patients with residual intestinal length greater than 50 cm, but it is significantly lower for patients with residual length less than 50 cm. (Buchman, The medical and surgical management of short bowel syndrome, *Med Gen Med* 2004: 6:12). In another study, the long-term survival was reported to be 45% in patients with a residual small intestine length less than 50 cm. (Warner, Tissue engineered small intestine: a viable clinical option? *Ann Surg* 2004:240(5):755-56). However, those with shorter residual intestine who survive are likely to develop liver and kidney failure and to remain totally dependent on PN. (Banerjee et al., Acute renal failure and metabolic disturbances in the short bowel syndrome, *Q J Med* 2002:95:37-40; Cavicchi et al., Prevalence of liver disease and contributing factors in patients receiving home parenteral nutrition for permanent intestinal failure, *Ann Intern Med* 2000:132:525-32).

The complex medical nature, management complications, and variable outcomes of SBS are not the only problems; there are other financial, social, and psychological impacts that add more complexity to the situation. SBS care is expensive and requires a long-term commitment by highly trained healthcare providers.

Accordingly, it is clear that there is an imminent need to find a curative solution for the debilitating and highly morbid disease of SBS that avoids, as much as possible, the many complications associated with existing treatment modalities.

SUMMARY

Certain embodiments of the disclosure concern devices and methods of increasing the length of a tubular organ, such as the large or small intestine, or the esophagus. In one representative embodiment, an implantable distraction device comprises a tubular member oriented along a longitudinal axis of the distraction device, a curved first attachment member coupled to the tubular member and configured to be sutured within a body lumen, and a curved second attachment member coupled to the tubular member and configured to be sutured within a body lumen. The second attachment member is spaced apart from the first attachment member along the tubular member. The device further comprises at least one magnet coupled to the tubular member and movable relative to the tubular member. At least one of the first attachment member or the second attachment member is axially movable relative to the other of the first attachment member or the second attachment member between a first position and a second position to vary an axial distance between the first and second attachment members. The at least one magnet is configured such that motion of a magnetic field relative to the distraction device causes corresponding motion of the at least one magnet, and corresponding motion of one attachment member relative to the other.

In some embodiments, the first attachment member is coupled to a first end portion of the tubular member.

In some embodiments, the implantable distraction device further comprises an annular actuator member movably disposed on the tubular member, and a plurality of magnets including the at least one magnet. The plurality of magnets are arrayed circumferentially around the actuator member.

In some embodiments, the tubular member comprises a channel extending along the length of the tubular member, and the actuator member comprises an engagement member configured to engage the channel such that the actuator member is movable along a path defined by the channel.

In some embodiments, the channel comprises a plurality of axially-extending channel portions interconnected by circumferentially-extending channel portions.

In some embodiments, the channel extends helically along the length of the tubular member.

In some embodiments, the channel comprises a plurality of first channel portions extending along the tubular member at an angle to the longitudinal axis of the distraction device, and the first channel portions are interconnected by second channel portions extending axially along the tubular member.

In some embodiments, the actuator member is positioned between the first attachment member and the second attachment member, and the actuator member is configured to engage the second attachment member such that axial motion of the actuator member along the tubular member causes corresponding axial motion of the second attachment member toward the second position.

In some embodiments, the first attachment member comprises an annular suture retention member configured to be sutured to a body lumen.

In some embodiments, the tubular member is configured as an extension member comprising a first tubular portion and a second portion telescopically movable relative to the first tubular portion, and the extension member extends between and is fixed to the first and second attachment members to vary the axial distance between the first and second attachment members.

In some embodiments, the first and second attachment members include a plurality of curved segments interconnected by flexible joints to form flexible rings.

In some embodiments, the plurality of extension members include respective first and second portions telescopically movable relative to each other.

In some embodiments, the distraction device further comprises a plurality of extension members extending between the first and second attachment members and arrayed circumferentially around the longitudinal axis of the distraction device.

In some embodiments, the plurality of extension members include ratchets that selectively permit extension but not retraction of the telescoping first and second portions.

In some embodiments, the distraction device further comprises an annular actuator member coupled to the extension members, and a plurality of magnets including the at least one magnet are arrayed circumferentially around the actuator member. The second portions of the extension members can include a plurality of engagement members spaced apart lengthwise along the second portions and configured to engage the actuator member to selectively permit extension of the extension members when the actuator member is rotated.

In some embodiments, the first and second attachment members define respective lumens through which suture may be inserted to secure the attachment members to a body lumen.

In some embodiments, the distraction device further comprises a housing coupled to the extension member, the housing including an actuator member movable within the housing between a first position in which the actuator member contacts the second member of the extension member to prevent axial movement of the second member relative to the first tubular member, and a second position in which the second member is movable relative to the first tubular member. The at least one magnet is coupled to the first actuator member such that application of a magnetic field to the first actuator member causes the first actuator member to move to the second position.

In another representative embodiment, a system comprises an implantable distraction device including a tubular member oriented along a longitudinal axis of the distraction device. The distraction device includes a curved first attachment member coupled to the tubular member and configured to be sutured within a body lumen, and a curved second attachment member coupled to the tubular member and configured to be sutured within a body lumen. The second attachment member is spaced apart from the first attachment member along the tubular member. The device further includes at least one magnet coupled to the tubular member and movable relative to the tubular member. At least one of the first attachment member or the second attachment member are axially movable relative to the other of the first attachment member or the second attachment member between a first position and a second position to vary an axial distance between the first and second attachment members. The at least one magnet is configured such that motion of a magnetic field relative to the distraction device causes corresponding motion of the at least one magnet, and corresponding motion of one attachment member relative to the other. The system further comprises a control device including a plurality of magnets configured to magnetically couple with the at least one magnet of the distraction device such that motion of the control device in a direction along a longitudinal axis of the distraction device, or motion of the control device perpendicular to the longitudinal axis of the distraction device, causes corresponding motion of one attachment member of the distraction device relative to the other.

In some embodiments, the control device comprises a housing, and the plurality of magnets are disposed linearly along a lower surface of the housing.

In some embodiments, the control device comprises a first magnetic coupling portion including a curved body having a first end face and a second end face, at least the first end face comprising a plurality of magnets. The plurality of magnets comprises a central magnet surrounded by an annular array of magnets, the magnets of the annular array having a polarity different from a polarity of the central magnet.

In another representative embodiment, a method comprises implanting a distraction device in a lumen of a patient's body, the distraction device including a tubular member oriented along a longitudinal axis of the distraction device, a curved first attachment member coupled to the tubular member and configured to be sutured within the body lumen, and a curved second attachment member coupled to the tubular member and configured to be sutured within the body lumen. The second attachment member is spaced apart from the first attachment member along the tubular member. The distraction device further comprises at least one magnet coupled to the tubular member and movable relative to the tubular member. At least one of the first attachment member or the second attachment member is axially movable relative to the other of the first attachment member or the second attachment member between a first position and a second position to vary an axial distance between the first and second attachment members. The at least one magnet is configured such that motion of a magnetic field relative to the distraction device causes corresponding motion of the at least one magnet, and corresponding motion of one attachment member relative to the other. The method further comprises attaching the first and second attachment members to the lumen of the patient's body, and applying a magnetic field to the at least one magnet of the distraction device from outside the lumen of the patient's body such that one attachment member moves longitudinally relative to the other attachment member to apply tension to tissue of the body lumen between the first and second attachment members.

In some embodiments, attaching the first and second attachment members further comprises suturing the first and second attachment members within the lumen of the patient's body.

In some embodiments, the distraction device further comprises an annular actuator member movably disposed on the tubular member, and the actuator member comprises a plurality of magnets including the at least one magnet arrayed circumferentially around the actuator member. The magnetic field is associated with a control device including a plurality of magnets configured to magnetically couple with the plurality of magnets of the actuator member, and moving the magnetic field further comprises moving the control device axially along the tubular member.

In some embodiments, the method is a distraction enterogenesis method and the lumen of the patient's body is an intestine.

In some embodiments, the intestine is a small intestine.

The foregoing and other objects, features, and advantages of the disclosed technology will become more apparent from the following detailed description, which proceeds with reference to the accompanying figures.

BRIEF DESCRIPTION OF THE DRAWINGS

FIGS. 39A-39C are magnified cross-sectional views illustrating operation of an actuator assembly coupled to the extension member of the distraction device of FIG. 38.

DETAILED DESCRIPTION

Figure 1:
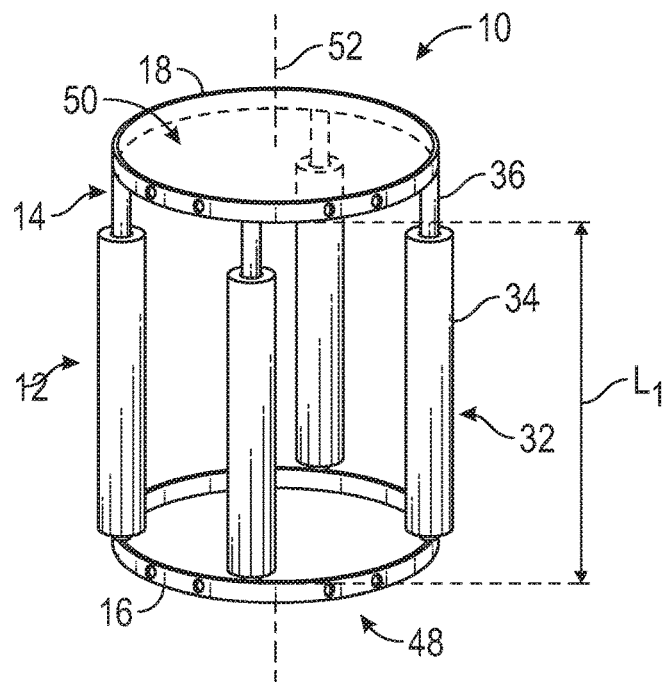
FIG. 1 is a perspective view of a representative embodiment of a telescopic distraction device in a retracted position.

The present disclosure concerns intraluminal and/or extraluminal devices that can be used to lengthen various lumens or organs of the body. For example, certain embodiments can be configured for implantation in the small intestine in order to lengthen the small intestine as a treatment for short bowel syndrome. The disclosed embodiments can allow full small intestine function during the lengthening process as they are open on both ends, and the walls are porous, or comprise relatively thin parts with spaces in between to allow absorption and peristaltic movement through and past the device without causing significant intestinal obstruction. Certain configurations can also accommodate the increased diameter of the small intestine as needed through a design that allows diameter expansion. In some embodiments, more than one device can be used (e.g., in series) to achieve faster results as the creation of blind-ended segments is not required, as with existing devices. In some embodiments, the device can be made of a biodegradable material so that a second procedure for retrieval of the device is not required. In other embodiments, if a second surgery is required (e.g., to close an ostomy or reanastomose the intestine, the disclosed devices can be used extraluminally. In certain configurations, the amount of distraction and/or the longitudinal mechanical force for lengthening of the organ, can be controlled from outside the body, for example, with a magnetic distraction system.

In certain examples, distraction enterogenesis (DEG) can provide a solution with low clinical, financial, and social complications. DEG is a process by which longitudinal mechanical forces are applied to induce lengthening of intestine to achieve greater surface area. (Koga et al., Distraction-induced intestinal enterogenesis: preservation of intestinal function and lengthening after reimplantation into normal jejunum. *Ann Surg*. 2012:255(2):302-10; Park et al., Enterogenesis by mechanical lengthening: morphology and function of the lengthened small intestine. *J Pediatr Surg* 2004:39(12):1823-7; Safford et al., Longitudinal mechanical tension induces growth in the small bowel of juvenile rats.

Gut 2005:54(8): 1085-90; Spencer et al., Enterogenesis in a clinically feasible model of mechanical small-bowel lengthening. Surgery 2006:140(2):212-20). The concept can be clinically successful in multiple tissues including bone, breast, esophagus, urethra, and in the aorta. (Al-Mandi et al., Clinical evaluation of distraction osteogenesis in the treatment of mandibular hypoplasia. *J Craniofac Surg* 2013; 24(1): e50-7; Eriksen et al., A prospective randomized study comparing two different expander approaches in implant-based breast reconstruction: one stage versus two stages. *Plast Reconstr Surg* 2012; 130(2):254e-64e; Mahour et al., Elongation of the upper pouch and delayed anatomic reconstruction in esophageal atresia. *J Pediatr Surg* 1974; 9(3): 373-83; Liu et al., Chronic urogenital sinus expansion in reconstruction of high persistent cloaca. *Pediatr Surg Int* 2012; 28(8):835-40; Kim et al., A novel treatment for the midaortic syndrome. *N Engl J Med* 2012; 367(24):2361-2).

Animal studies showed that controlled tension can yield multifold lengthening with normal intestinal function and sustained lengthening after device removal. (Koga et al., Distraction-induced intestinal enterogenesis: preservation of intestinal function and lengthening after reimplantation into normal jejunum. *Ann Surg*. 2012:255(2):302-10; Sullins et al., Function of mechanically lengthened jejunum after restoration into continuity. J Pediatr Surg 2014:49(6):971-4; Okawada et al., Distraction-induced enterogenesis: a unique mouse model using polyethylene glycol. *J Surg Res* 2011: 170(1):41-7). Increased intestinal length can be accompanied by mesenteric revascularization, muscular hypertrophy, increased mucosal surface area, and increased epithelial cell proliferation. (Safford et al., Longitudinal mechanical tension induces growth in the small bowel of juvenile rats. *Gut* 2005:54(8): 1085-90; Okawada et al., Distraction-induced enterogenesis: a unique mouse model using polyethylene glycol. *J Surg Res* 2011:170(1):41-7; Ralls et al., Mesenteric neovascularization with distraction-induced intestinal growth: enterogenesis. *Pediatr Surg Int.* 2013:29(1):33-9). Intestinal length can be an important factor in predicting SBS patients' outcomes, as mentioned earlier, and appropriate length can help resume enteral nutrition, which can improve the survival rates and quality of life dramatically. (Weih et al., Current practice and future perspectives in the treatment of short bowel syndrome in children—a systemic review. *Langenbecks Arch Surg* 2012:397:1043-51; Buchman, The medical and surgical management of short bowel syndrome. *Med Gen Med* 2004:6:12; Warner, Tissue engineered small intestine: a viable clinical option? *Ann Surg* 2004:240(5):755-56).

Various Intraluminal and extraluminal methods of lengthening using DEG have been proposed. These methods include fluid injection, osmotic distension, hydraulic pistons, extracorporeal screws, extracorporeal catheter, extraluminal helicoidal stretch, and spring devices. (Koga H, Sun X, Yang et al., Distraction-induced intestinal enterogenesis: preservation of intestinal function and lengthening after reimplantation into normal jejunum. *Ann Surg.* 2012:255(2): 302-10; Park et al., Enterogenesis by mechanical lengthening: morphology and function of the lengthened small intestine. *J Pediatr Surg* 2004:39(12):1823-7; Okawada et al., Distraction-induced enterogenesis: a unique mouse model using polyethylene glycol. *J Surg Res* 2011:170(1): 41-7; Ralls et al., Mesenteric neovascularization with distraction-induced intestinal growth: enterogenesis. *Pediatr Surg Int.* 2013:29(1):33-9; Stark et al., Development of an endoluminal intestinal lengthening capsule. *J Pediatr Surg*. Elsevier Inc. 2012:47(1): 136-41.; Sueyoshi et al., Glucagon-Like peptide 2 increases efficacy of distraction enterogenesis. *J Surg Res* 2013:184(1):365-73; Demehri et al., Development of an edoluminal intestinal lengthening device using a geometric intestinal attachment approach. *Surgery* 2015:158(3):802-11; Dionigi et al., Extraluminal helicoidal stretch (Helixtretch): A novel intestinal lengthening. *J Pediatr Surg* 2014:49:1787-90; Sullins et al., A novel biodegradable device for intestinal lengthening. *J Pediatr Surg* 2014: 49:109-13). However, each of these models has multiple limitations.

For example, fluid injection (e.g., saline) often requires multiple surgical procedures, the creation of a closed loop, and may be ineffective (e.g., due to rapid saline absorption). Osmotic distention also requires multiple surgical procedures, the creation of a closed loop, and the use of a percutaneous pump. Hydraulic pistons, extracorporeal screws, and extracorporeal catheters require multiple surgical procedures, the creation of a blind loop, and can be associated with dislodgement of the device, infection, fistula formation, perforation, and/or adhesions. Extraluminal helicoidal stretch procedures can also require multiple surgeries, blind loop creation, and are associated with technical difficulties, lengthy procedures, and peritoneal reactions. Spring devices require multiple surgical procedures, provide uncontrolled distraction forces, and complications can include buckling or migration of the device, and/or perforation of the bowel.

As SBS patients do not have enough length for further loss, models that require closed or blind loop creation may not be feasible. Repeated surgical procedures, to implant and retrieve lengthening devices, or to restore intestinal continuity may lead to significant loss of intestinal length, increased risk of surgery-related injury, and/or risk of elevated systemic inflammatory response of SBS patients due to laparotomy. (Chawla et al., Profound systemic inflammatory response syndrome following non-emergent intestinal surgery in children. *J Pediatr Surg* 2013:48(9): 1936-40).

Figure 2:
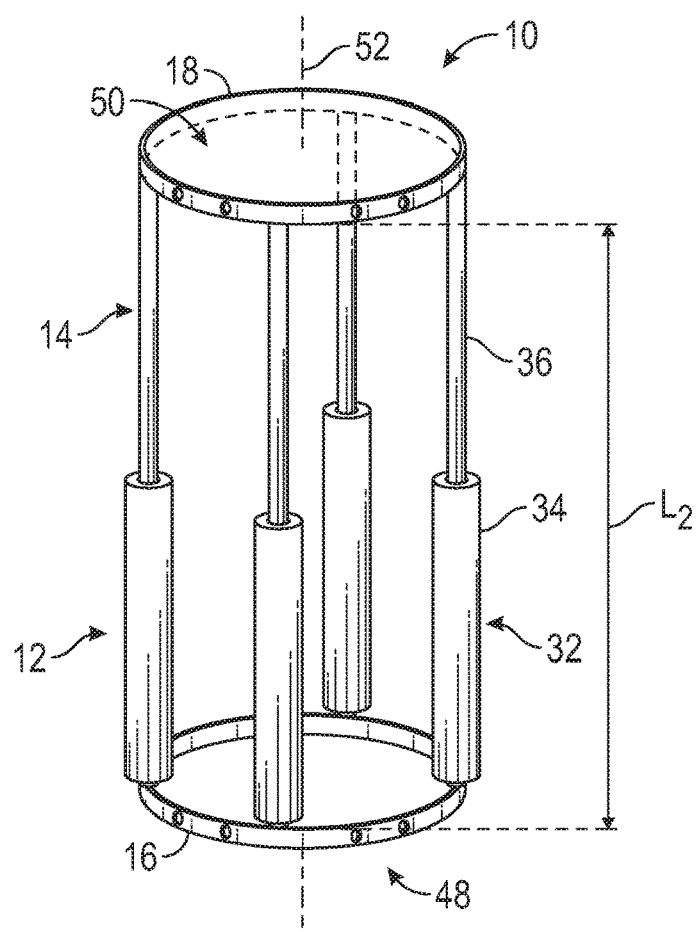
FIG. 2 is a perspective view of the distraction device of FIG. 1 in an extended position.

Referring to the figures, FIG. 1 illustrates a representative embodiment of a distraction device 10 configured to be implanted in a lumen of the body, or outside or around the body lumen, such as the small intestine, and configured to reduce the complications associated with existing treatments for short bowel syndrome. The device 10 can include a cylindrical main body having a first portion generally indicated at 12, and a second portion generally indicated at 14. The first and second portions 12, 14 can be configured to move longitudinally relative to one another along a longitudinal axis 52 of the device that extends in a direction of extension of the device. The device is capable of extending from a first or initial retracted length $L_1$ (FIG. 1) to a second or extended length L2 (FIG. 2) to selectively increase or decrease the overall length of the device.

The first portion 12 can include a curved first attachment member 16, and the second portion 14 can include a curved second attachment member 18. In the illustrated embodiment, the first and second attachment members 16, 18 are configured as collars or rings, and circumscribe respective central openings 48, 50. The annular nature of the attachment members 16, 18 can allow the device to be implanted in a body lumen without obstructing the lumen. In other embodiments, the attachment members may also be semi-circular, or any other suitable shape, as desired.

Figure 3:
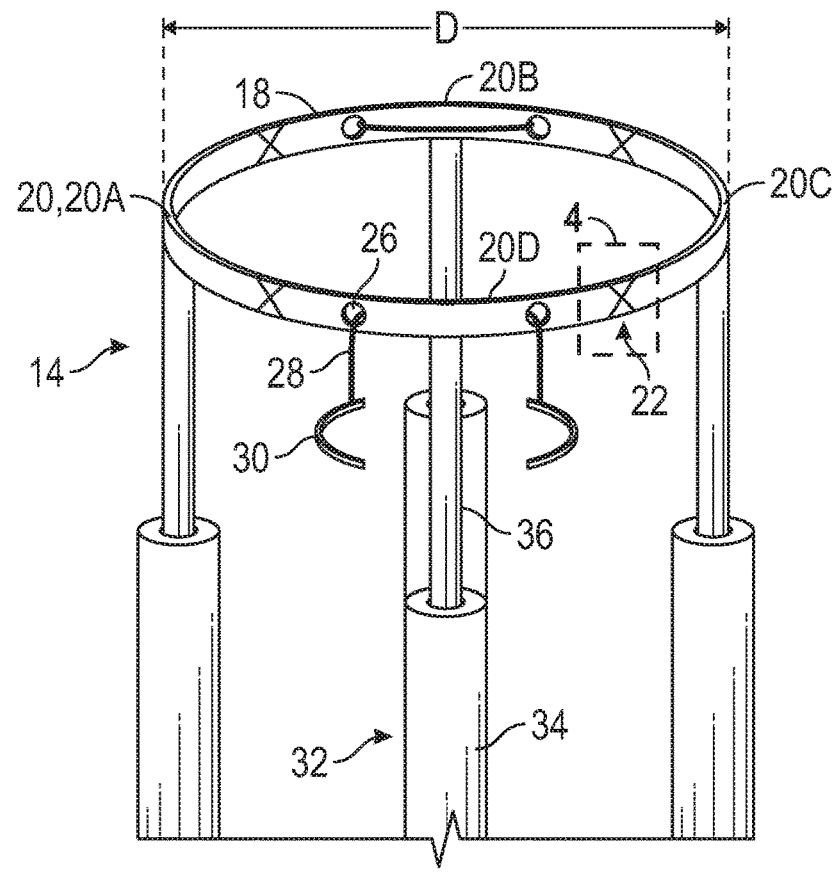
FIG. 3 is a perspective view of an attachment member of the distraction device of FIG. 1.
Figure 4:
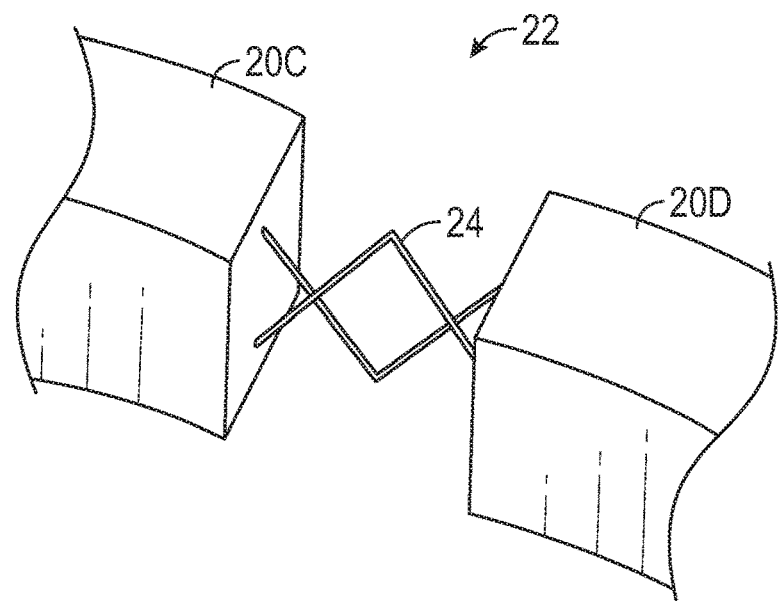
FIG. 4 is a perspective detail view of a flexible coupling of the attachment member of FIG. 3.
Figure 5:
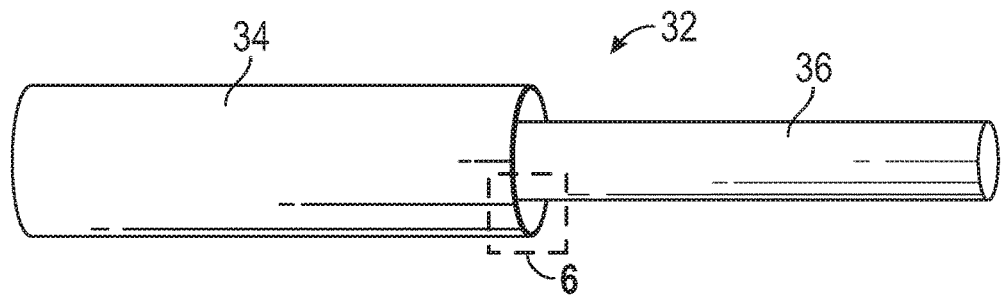
FIG. 5 is a perspective view of an extension member of the distraction device of FIG. 1.

With reference to FIGS. 3 and 4, the attachment members can include a plurality of curved segments or portions 20 interconnected by flexible joints 22. For example, in the illustrated embodiment, the first attachment member 16 includes four portions 20A-20D, although the attachment members can include more or fewer portions, as desired.

The flexible joints 22 can allow the portions 20A-20D to move relative to each other. For example, the portions 20A-20D can move radially inwardly or outwardly to change a diameter D of the first attachment member 16 (e.g., to allow it to adjust to the diameter of a lumen into which the device is implanted). The joints 22 can also allow the portions 20A-20D to move longitudinally or angularly to accommodate, for example, curves in the anatomy of the organ in which the device is implanted. The joints also permit reversible expansion and contraction of the rings to accommodate the flow of intestinal contents during digestion, mimicking the changing diameter of the intestinal lumen in response to such flow. In the illustrated embodiment, the joints 22 can include spring members such as spring member 24 shown in FIG. 4. In other embodiments, the joints 22 can include any suitably flexible construction, such as flexible polymeric couplings, sutures, shape-memory alloys, springs, etc.

Referring again to FIG. 3, the attachment member 18 can define openings 26 through which suture 28 can be loaded prior to implantation. In certain configurations, the suture 28 can be a "double armed" suture, with a needle 30 secured to each end of the suture. In the illustrated embodiment, the segments 20A-20D can be hollow such that the attachment member 18 defines an interior lumen or passage around the circumference of the attachment member through the segments. In the illustrated configuration, the suture 28 can extend around the circumference of the attachment member 18 through the lumen, and the ends of the suture including the needles 30 can extend from adjacent openings 26. In the illustrated configuration, the attachment member 16 can have a similar structure and function.

In certain embodiments, one or more of the portions 20A-20D of the first and second attachment members can be ferromagnetic or magnetic. In other embodiments, the first and second attachment members 16, 18 can include one or more magnets (e.g., coupled to the portions 20A-20D). This can allow the device to be coupled with or acted upon by a magnetic field applied from outside the body to manipulate the length of the device, as further described below.

Referring again to FIGS. 1 and 2, the first and second attachment members 16, 18 can be coupled together by a plurality of extension members 32. In the illustrated configuration, the extension members 32 include concentric tubular members or portions, such as a larger diameter first portion 34 and a second lesser diameter portion 36. The second portion 36 can therefore be disposed coaxially within and movable relative to the first portion 34 in a telescoping manner between a retracted position (FIG. 1) corresponding to the initial shorter length L₁ of the device and an extended position (FIG. 2) corresponding to the second extended length L2.

In the illustrated embodiment, the device includes four extension members 32 arrayed substantially parallel to one another about the circumferences of the first and second attachment members 16, 18, and angularly spaced from one another by about 90 degrees. In other embodiments, the device can include more or fewer extension members spaced at any suitable angular spacing. In particular embodiments, there are a plurality of extension members 32, for example two, three, or four. In the illustrated configuration, the spaces between the extension members 32 are open. However, in other embodiments the device 10 can include a covering (e.g., a porous or non-porous covering) disposed around the extension members 32 to enclose the lumen of the device 10.

Figure 6:
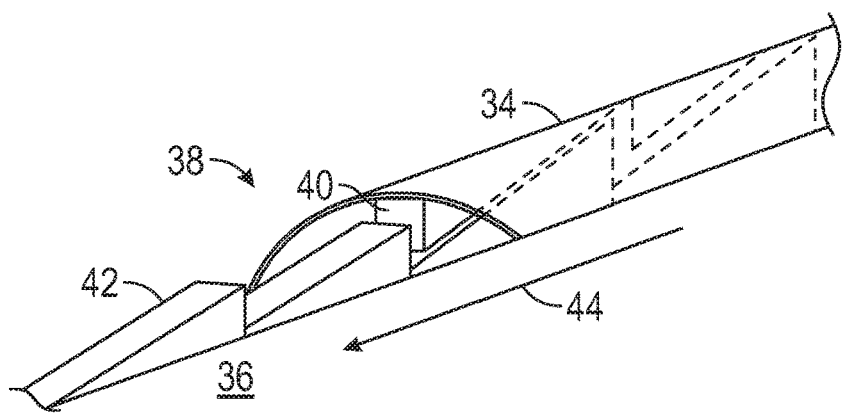
FIGS. 6-8 are magnified perspective views of motion-limiting mechanisms of the extension member of FIG. 5.
Figure 7:
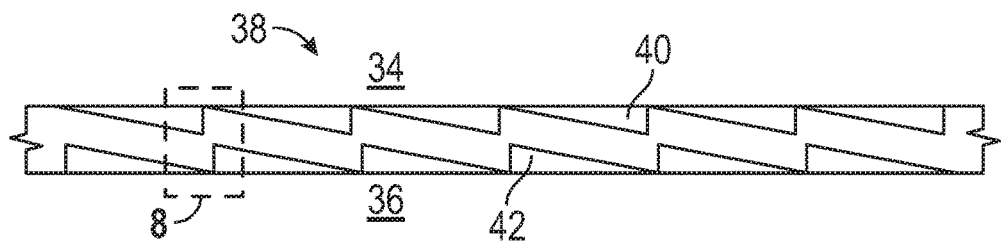
Figure 8:
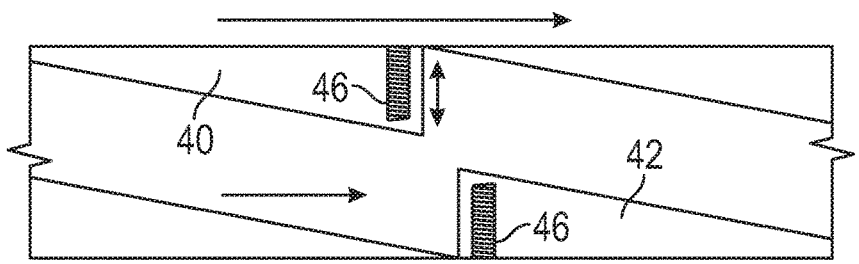

In some configurations, the extension members 32 can include motion-limiting mechanisms configured to selectively permit motion of the second portions 36 in one direction to permit extension or lengthening of the extension members, but not retraction or shortening. For example, with reference to FIGS. 5-8, the extension members 32 can include a motion-limiting mechanism configured as a ratchet generally indicated at 38, and configured to selectively permit motion of the second portion 36 outwardly from the first portion 34 while preventing the second portion from retracting back within the first portion. In the illustrated configuration, the first portion 34 can include on its internal surface a plurality of angled ribs or teeth 40 configured to engage a plurality of corresponding teeth 42 on an external surface of the second portion 36. The teeth 40 and 42 can be angled or wedge-shaped such that motion in the direction of arrow 44 (FIG. 6) (e.g., extension) is permitted, but motion in the opposite direction is prevented by abutment of adjacent teeth 40 and 42.

In some embodiments, the teeth 40 and/or the teeth 42 can be spring-biased to facilitate motion of the teeth past one another in the permitted direction of motion. For example, in the embodiment of FIG. 8, the teeth 40 and 42 can include spring members 46 disposed beneath apices of the teeth to provide resiliency to the teeth. In other embodiments, the motion-limiting mechanism can include a spring-biased latching member coupled to the first portion 34 and configured to engage a plurality of teeth located on the second portion 36, or vice versa.

Figure 9:
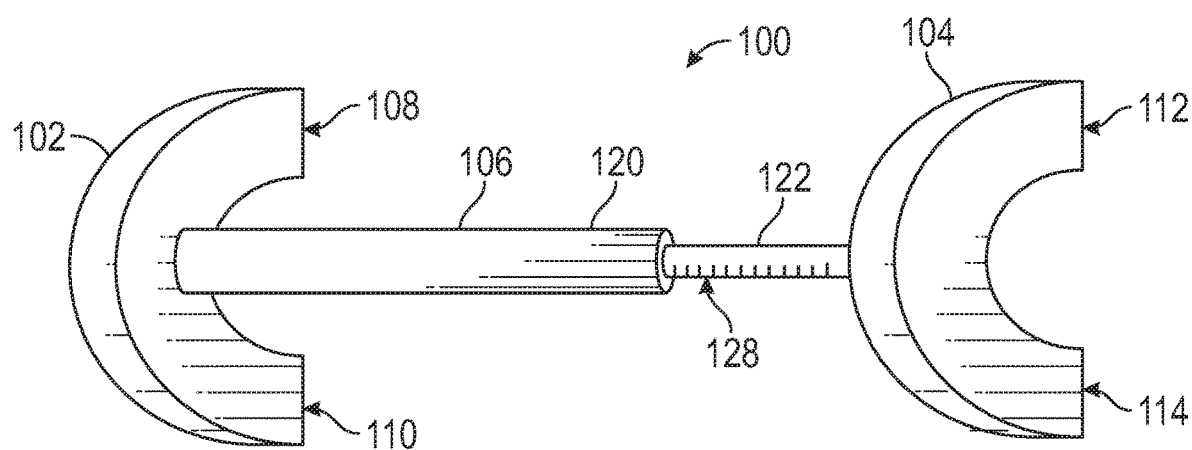
FIG. 9 is a perspective view of a representative embodiment of a magnetic controller device for selectively extending the length of a distraction device.

When implanted in a body lumen, the distraction device 10 can be manipulated remotely (e.g., magnetically) from outside the body to apply force to the lumen to gradually lengthen the lumen and promote tissue genesis. FIG. 9 illustrates a representative embodiment of a control device 100 that can be used to remotely extend the distraction device 10 from outside the body, for example, by magnetic interaction between the distraction device 10 and control device 100. In one disclosed embodiment, the control device 100 includes a first magnetic coupling member 102, a second magnetic coupling member 104, and an extendable member 106 disposed therebetween to hold the members 102 and 104 in a selected spacing relative to each other. In the illustrated embodiment, the extendable member 106 is configured as a telescoping body including a first portion 120 and a second portion 122 coaxially disposed within and movable relative to the first portion 120 between a retracted position and an extended position. Motion of the second portion 122 between the extended position and the retracted position causes corresponding motion of the second magnetic coupling member 104, allowing a user to selectively vary the distance between the first and second magnetic coupling members 102, 104, for example, in controlled increments.

In the illustrated configuration, the magnetic coupling members 102, 104 comprise curved (e.g., semi-circular or C-shaped) bodies including first and second end faces oriented parallel to each other. For example, with reference to FIGS. 9-11, the first magnetic coupling member 102 can include a first end face 108 and a second end face 110, and the second magnetic coupling member 104 can include a first end face 112 and a second end face 114.

Figure 10:
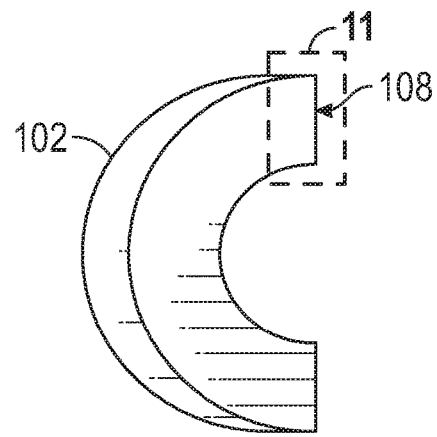
FIG. 10 is a perspective view of one end portion of the magnetic controller of FIG. 9.
Figure 11:
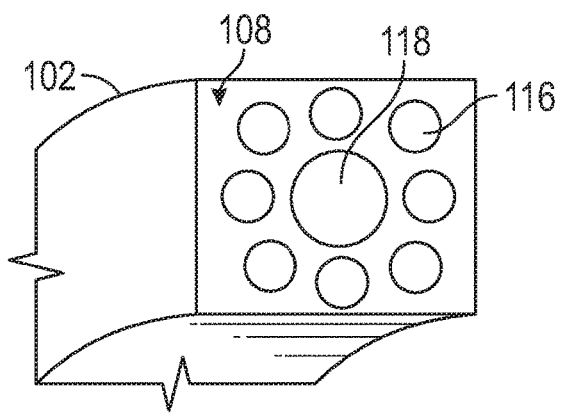
FIG. 11 is an enlarged perspective view of an end surface of the end portion of the magnetic controller shown in FIG. 10.

FIGS. 10 and 11 illustrate the first magnetic coupling member 102 and the first end face 108 in greater detail. Referring to FIG. 11, the end face 108 can include a plurality of magnets arrayed in an annular arrangement. For example, in the illustrated configuration, the end face 108 can include a plurality of first magnets 116 surrounding a second central magnet 118 that is larger than the first magnets. In certain configurations, the first and second magnets 116, 118 can have opposite polarities. In the illustrated embodiment, the end face 108 includes eight magnets 116 and one magnet 118, although the surface can have any suitable number of magnets 116 and/or 118 arranged in any suitable arrangement. In some embodiments, the second end face 110 of the first magnetic coupling member 102, and end faces 112, 114 of the second magnetic coupling member 104 can include magnet arrays similar to the magnet array of the end face 108. The magnets 116 and 118 can allow the control device 100 to magnetically couple with the distraction device 10 and non-invasively manipulate the distraction device after implantation in a patient's body.

Figure 12:
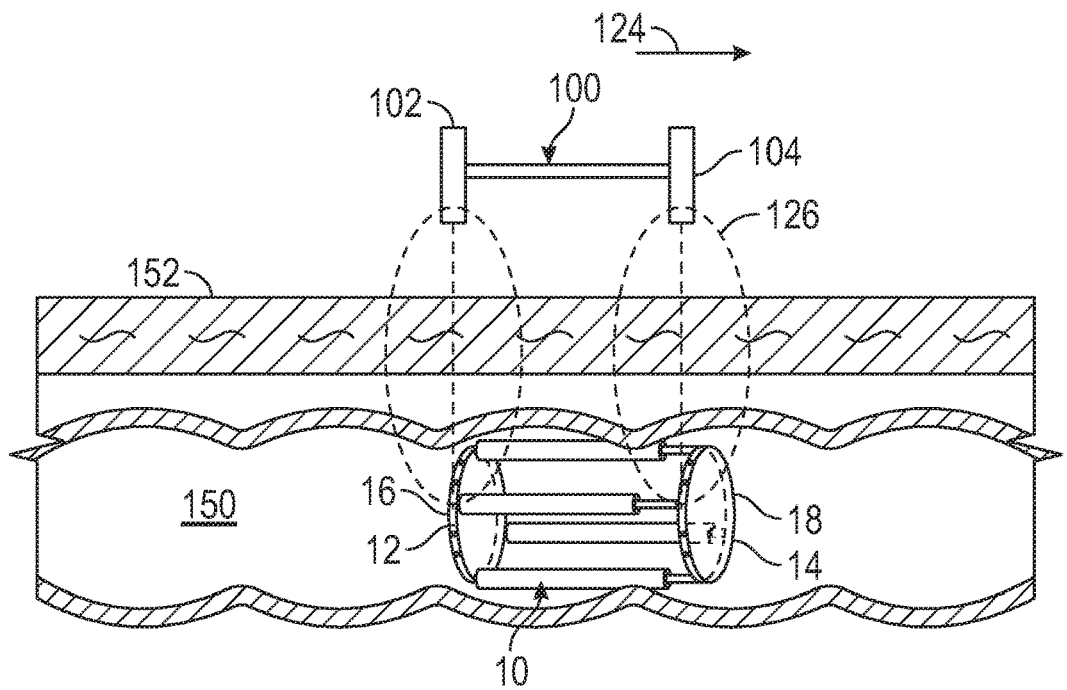
FIG. 12 is a cross-sectional view illustrating the distraction device of FIG. 1 implanted in the lumen of the small intestine and interacting with a magnetic field of the magnetic controller of FIG. 9 applied from outside the body to extend telescopic legs of the distraction device.
Figure 13A:
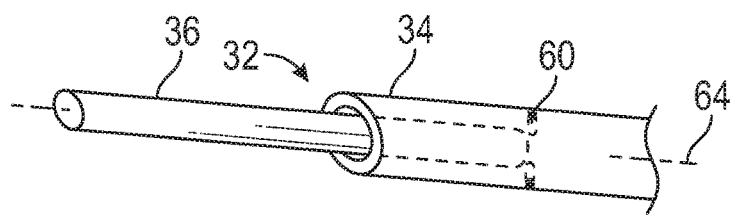
FIG. 13A is a perspective view of an extension member illustrating another embodiment of a motion-limiting mechanism including a plurality of pins.
Figure 13B:
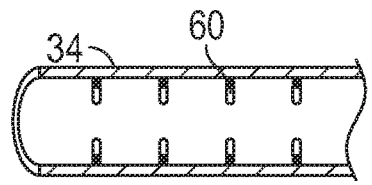
FIG. 13B is a partial cross-sectional view of a first portion of the extension member of FIG. 13A illustrating a plurality of pins.

Turning now to methods of use, the distraction device 10 can be configured for implantation in a surgical procedure, such as in a resection of the large intestine or the small intestine. For example, with reference to FIG. 12, the distraction device 10 can be positioned in the lumen of a bowel 150 with the device 10 in the retracted configuration. The first and second attachment members 16 and 18 can be sutured to the bowel wall using the preloaded sutures 28 (FIG. 3). After resection, the remaining portions of the small intestine can be anastomosed with the distraction device 10 located within the lumen of the bowel. The distraction device 10 may be located proximal, distal, or extending across the anastomosis depending upon, for example, the location of the resected portion along the length of the bowel 150 or constraints imposed by the surrounding anatomy.

After implantation of the distraction device 10 in a patient, the control device 100 can be positioned on or near the patient's body adjacent, but spaced apart from, the implanted distraction device 10 external to the abdominal wall 152. When positioned adjacent the distraction device 10, the first magnetic coupling member 102 can magnetically couple with the first portion 12 of the distraction device 10 (e.g., with the first attachment member 16), and the second magnetic coupling member 104 can magnetically couple with the second portion 14 (e.g., with the second attachment member 18) from outside the patient's body (note magnetic field lines generally indicated at 126). The magnetic coupling member 104 can then be advanced toward the extended position in the direction of arrow 124 while the magnetic coupling member 102 remains stationary (or vice versa). This can cause corresponding motion of the second attachment member 18 within the bowel 150 toward the extended position, lengthening the distraction device 10 and applying force to the bowel to promote enterogenesis. In certain configurations, the motion-limiting mechanisms 38 of the extension members 32 can prevent the distraction device 10 from shortening once the influence of the control device 100 is removed.

In certain embodiments, the control device 100 and/or the distraction device 10 can be configured to move between the retracted position and the extended position in predetermined increments. For example, in the case of the small intestine, the control device 100 and the distraction device 10 can be configured to lengthen from the retracted position toward the extended position in increments of 0.5 mm. In an exemplary embodiment wherein the initial length $L_1$ of the distraction device 10 is 5.5 cm, the control device 100 can be used to lengthen the distraction device 10 by 0.5 mm per day such that a fully extended length $L_2$ of 10.5 cm is reached after ten days, resulting in 5 cm of bowel lengthening. As illustrated in FIG. 9, in certain embodiments the second portion 122 of the extendable member 106 can include a scale or gradations generally indicated at 128 to aid the user in determining the amount of lengthening imparted to the device 10. In certain configurations, the gradations 128 can be radiopaque.

In certain configurations, components of the distraction device 10 such as the attachment members 16 and 18, the extension members 32, etc., can be made from biodegradable materials (e.g., polycaprolactone). The sutures 28 may also be made of biodegradable materials. In this manner, the device 10 can be configured to naturally breakdown during or after the lengthening treatment, obviating the need for a second surgical procedure to remove the device. In other embodiments, the distraction device 10 can be made from any other suitable biocompatible polymers or metals, such as stainless steel. In certain embodiments, any parts of the distraction device 10 not made from biodegradable material may be made sufficiently small such that they can pass through the bowel without requiring surgical retrieval.

The disclosed embodiments can provide significant advantages over known soft tissue distraction devices. For example, because the disclosed distraction device embodiments are open at each end, the device can be implanted intraluminally within the small intestine without obstructing the intestine, allowing full function of the small intestine over the course of the enterogenesis treatment. Additionally, because the distraction device is open at both ends, the disclosed embodiments do not require the creation of closed or blind loops in the small intestine. The flexible nature of the attachment members 16, 18 can also allow the device 10 to accommodate changes in the diameter of the small intestine. The disclosed device also reduces the number of surgical procedures required because various components of the device can be configured to biodegrade such that any remaining components exit the body via natural bowel function, and need not be retrieved surgically.

In some embodiments, multiple distraction devices 10 can be implanted at the same time (e.g., in series with one another at different locations within the small intestine) in order to achieve greater lengthening of the intestine than can be achieved with a single device. In other configurations, the distraction device embodiments described herein can also be adapted for use with the large intestine, with other tissues such as bone tissue, breast tissue, etc., or with other body lumens, such as the esophagus, the urethra, blood vessels such as the aorta, etc.

Figure 14A:
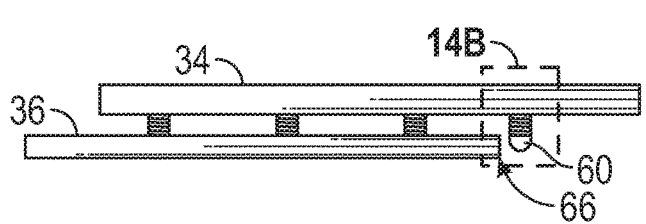
FIG. 14A is a cross-sectional view of the extension member of FIG. 13A illustrating the interaction of the pins with the second portion.
Figure 14B:
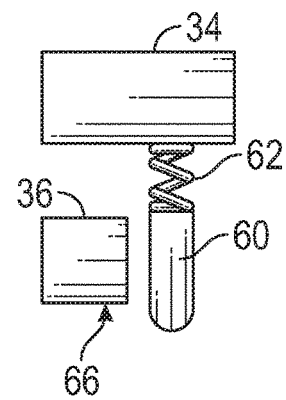
FIG. 14B is an enlarged view of the pin indicated in FIG. 14A.

FIGS. 13A-13B and 14A-14B illustrate another embodiment of a motion-limiting mechanism including a plurality of spring-biased pins 60. For example, with reference to FIGS. 13A and 13B, the first portion 36 of the extension member 32 can include a plurality of pins 60 arranged in one or more rows (e.g., two rows) extending lengthwise along the first portion. As shown in FIGS. 14A and 14B, the pins 60 can be coupled to the inner diameter of the first portion 36 by spring members 62 (FIG. 14B), and can be movable between a first radially outward position and a second radially inward position. In the illustrated embodiment, the springs 62 can bias the pins 60 radially inwardly toward the second position and toward a longitudinal axis 64 of the extension member 32.

As illustrated in FIG. 14A, when the second portion 36 of the extension member 32 is received within the first portion 34, the outer surface of the second portion 36 can urge the pins 60 radially outwardly toward the first position, thereby compressing the springs 62. As the second portion 36 moves telescopically out of the first portion 34 (e.g., to the left in FIG. 14A), an end portion 66 of the second portion 36 moves relative to the pins 60. After the end portion 66 passes a pin 60, the pin can move to the second position under action of the spring member 62, as shown in FIGS. 14A and 14B. Once in the second position, the pin 60 can block movement of the second portion back inside the first portion 34.

In certain configurations, the pins 60 can be spaced apart from each other at increments corresponding to a selected amount of lengthening of the distraction device, such as 1 mm, 2 mm, 5 mm, 10 mm, etc. In some embodiments, the first portions 34 of the extension members 32 can include one row of pins, two rows of pins, or any other suitable number of rows. In other configurations, the pins 60 can be coupled to the second portion 36 and configured to engage, for example, teeth such as the teeth 40 of FIGS. 6-8, or other corresponding features on the inner surfaces of the first portions 34 (e.g., detents).

Figure 15:
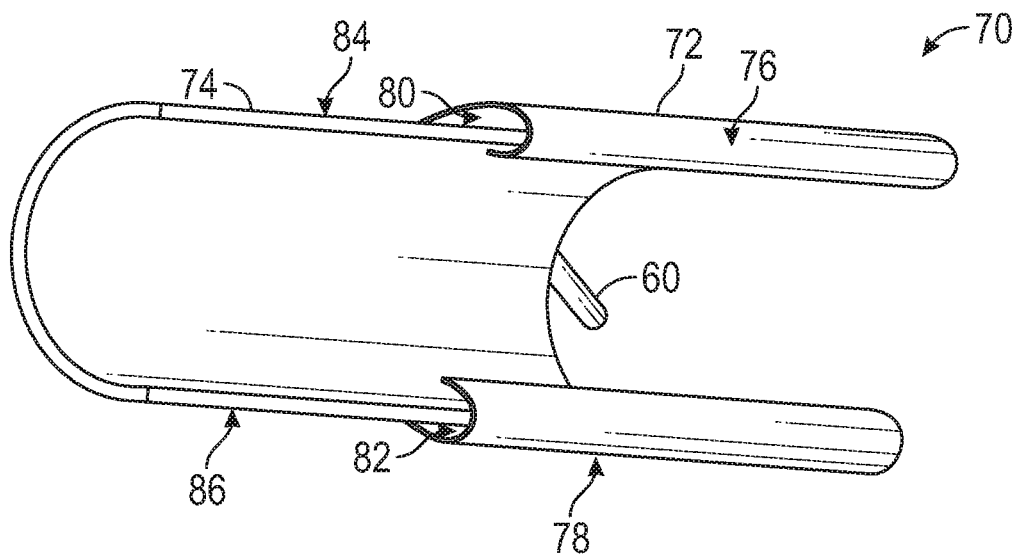
FIG. 15 is a perspective view of another embodiment of an extension member that can be used in combination with any of the distraction device embodiments described herein.

FIG. 15 shows another configuration of an extension member 70 including telescoping first and second portions 72, 74 configured as concave semi-cylindrical members that are open lengthwise on one side. In the illustrated configuration, longitudinal edge portions 76, 78 of the first portion 72 can be folded to form respective cuffs or channels 80, 82. Edge portions 84, 86 of the second portion 74 can be slidably received in the channels 80, 82 of the first portion such that the first and second portions can move telescopically relative to each other, as described above. In the illustrated embodiment, the first portion 72 can include one or more pins 60 to restrict inward movement of the second portion 74 relative to the first portion, as described above with respect to FIGS. 13A-13B and 14A-14B. The distraction device 10 can include one or more extension members 70 in lieu of, or in combination with, the extension members 32 described above. In some embodiments, the extension members 72 can be arranged such that the convex surfaces of the first and second portions 72, 74 are oriented outwardly in the direction of the wall of a body lumen into which the distraction device is implanted.

Figure 16A:
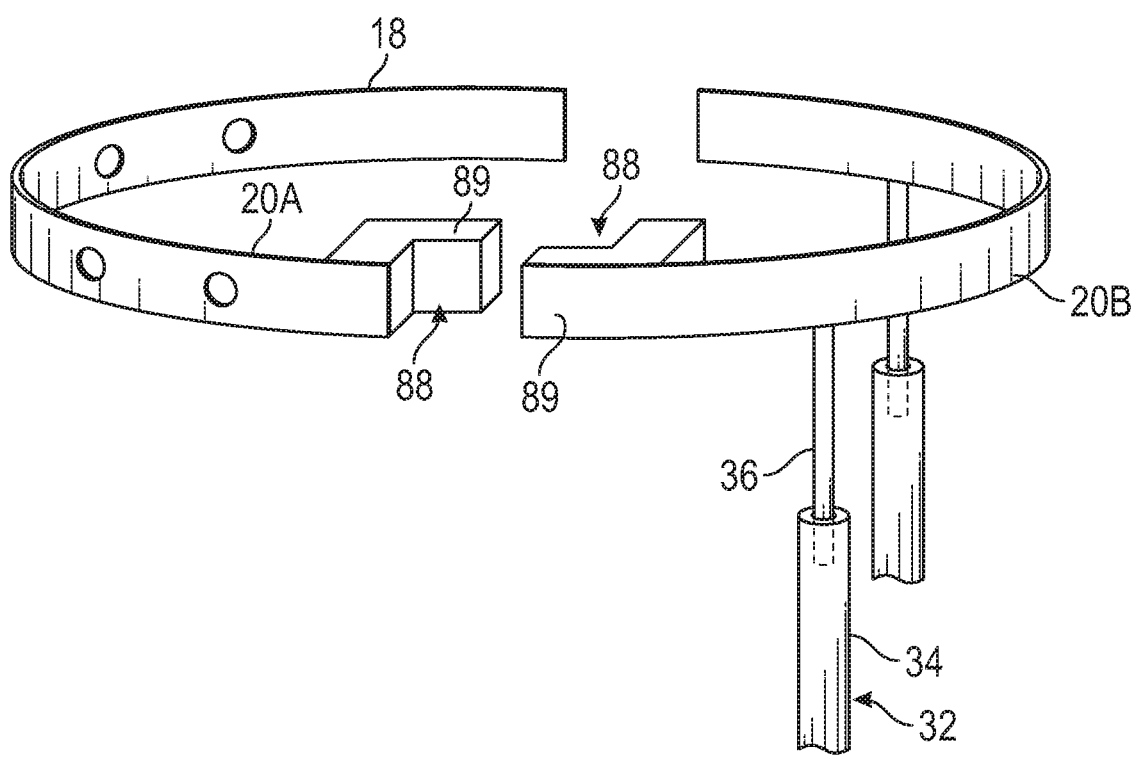
FIGS. 16A and 16B are perspective views illustrating another embodiment of a joint including recesses and corresponding projections for coupling together segments of an attachment member.
Figure 16B:
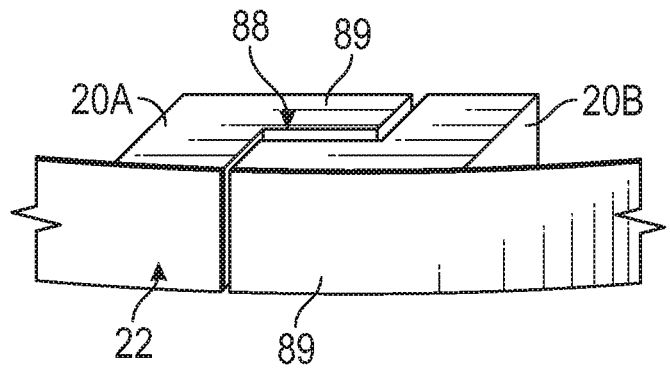

FIGS. 16A and 16B illustrate another configuration of the joints 22 by which the segments 20 of the attachment members 16 and 18 can be coupled to one another. In the illustrated configuration, end portions of adjacent segments 20A and 20B can include notches, cutouts, or recesses 88, and extension portions 89. The recess 88 and the extension portion 89 on the segment 20A can be offset (e.g., radially) from the corresponding recess 88 and extension portion 89 on the segment 20B. In this manner, the extension portions 89 can be received in the respective recesses 88 such that the extension portions engage or interlock with each other, as shown in FIG. 16B. This can limit transverse motion of the segments 20A and 20B relative to one another, while allowing, for example, longitudinal motion and/or radial motion.

Figure 17A:
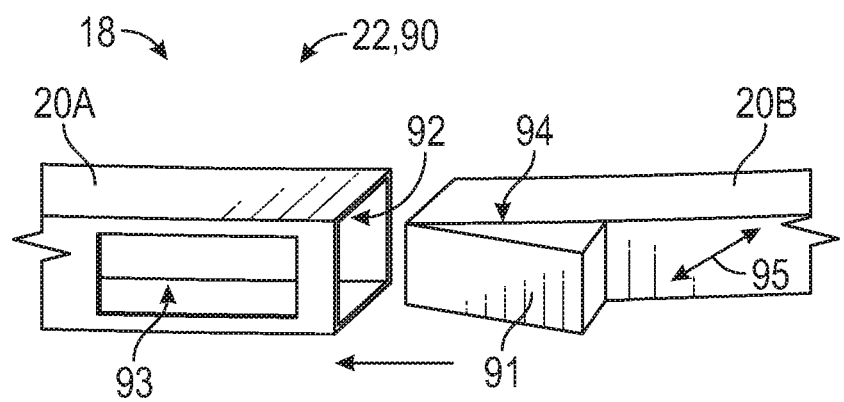
FIGS. 17A and 17B are perspective views illustrating another embodiment of a joint including a buckle for coupling together segments of an attachment member.
Figure 17B:
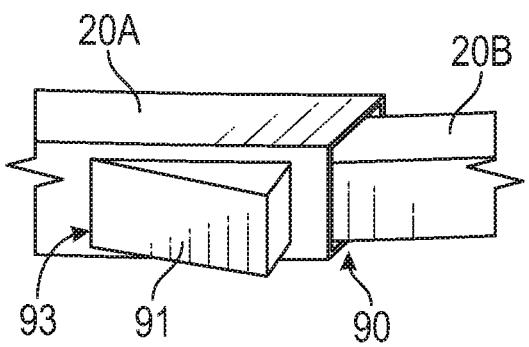

Referring to FIGS. 17A and 17B, the joints 22 can also comprise buckles 90. For example, referring to FIG. 17A, one end portion of a segment 20B of an attachment member 18 can include a male portion having a spring-biased wedge-shaped retainer configured as a latching member 91. In some embodiments, the latching member 91 can be retracted into a recess 94 within the segment 20B, and can be movable against and with its spring bias into and out of the segment 20B in the direction of arrow 95. In the disclosed configuration, the latching member 91 can be spring-biased toward the extended position. An end surface of the adjacent segment 20A can define a first opening 92 in communication with the lumen of the attachment member 18. The segment 20A can further comprise a second opening 93 on an outer surface of the segment 20A. When the latching member 91 is inserted into the opening 92, the segment 20A can contact an inclined face of the wedge-shaped latching member 91 and push it inwardly into the segment 20B until a top surface of the wedge-shaped member is flush with the outer surface of the segment 20B. When the latching member 91 has been advanced into the segment 20A such that the latching member 91 lines up with the second opening 93, the retracted latching member 91 can spring back to the extended position, and can extend through the opening 93 such that a rear face of the latching member 91 is captured by and retained within the segment 20A, as shown in FIG. 17B.

Figure 18:
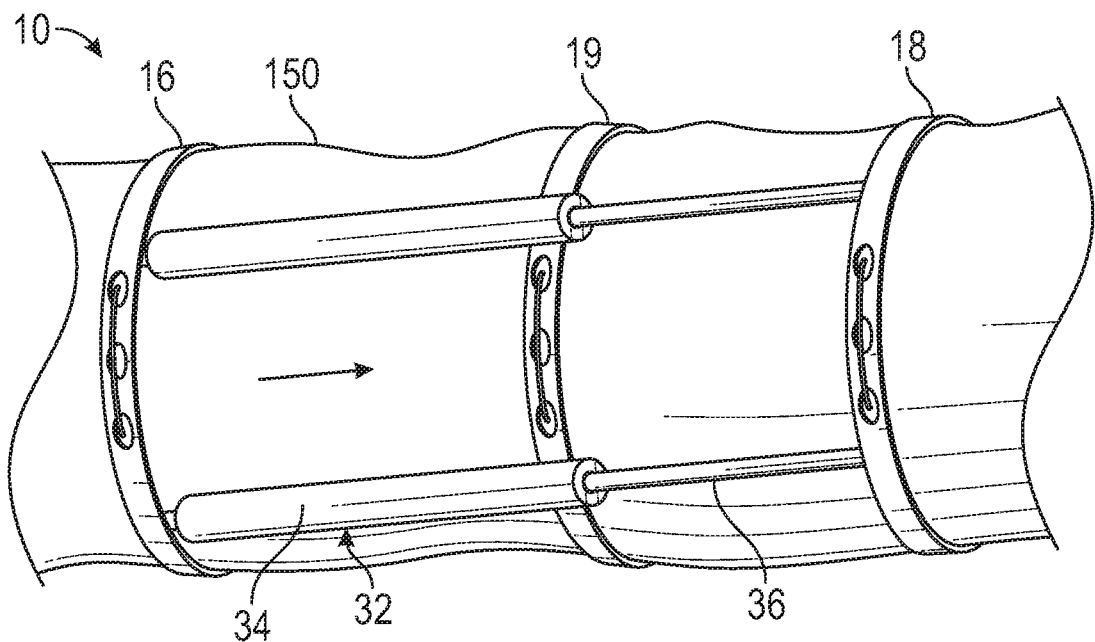
FIG. 18 is a schematic side elevation view illustrating another embodiment of a distraction device configured to be placed extraluminally around the intestine.

In certain configurations, the disclosed distraction devices can also be placed around the intestine extraluminally, as shown in FIG. 18. In the embodiment illustrated in FIG. 18, the distraction device 10 can be sutured to the outer diameter of the intestine 150 with the pre-loaded sutures 28, and can include a third attachment member 19 disposed between the attachment members 16 and 18. In the illustrated configuration, the third attachment member 19 can be located near the ends of the first portions 34 of the extension members 32 from which the second portions 36 extend.

Figure 19:
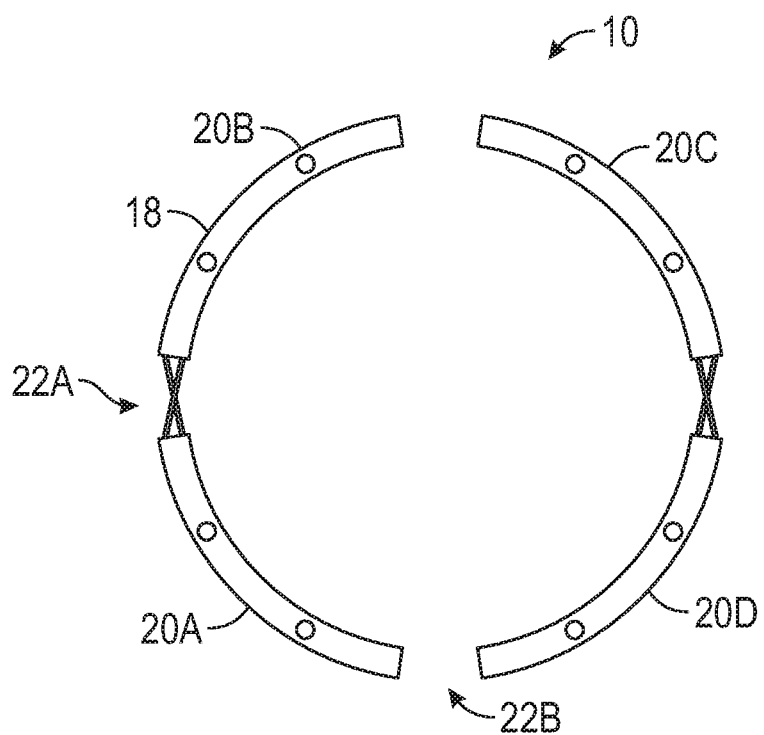
FIG. 19 is an end view of the distraction device of FIG. 18.

FIG. 19 is a side elevational end view of the distraction device 10 of FIG. 18. In the embodiment of FIG. 19, the segments 20A and 20B can be coupled together by movable or flexible connections 22A, such as any of the flexible joint embodiments described above. The segments 20C and 20D can also be coupled in this manner. Meanwhile, the segments 20B and 20C and the segments 20A and 20D can be coupled by less flexible or rigid connections 22B, such as by any of the joints 22 illustrated in FIGS. 16A-17B.

Figure 20:
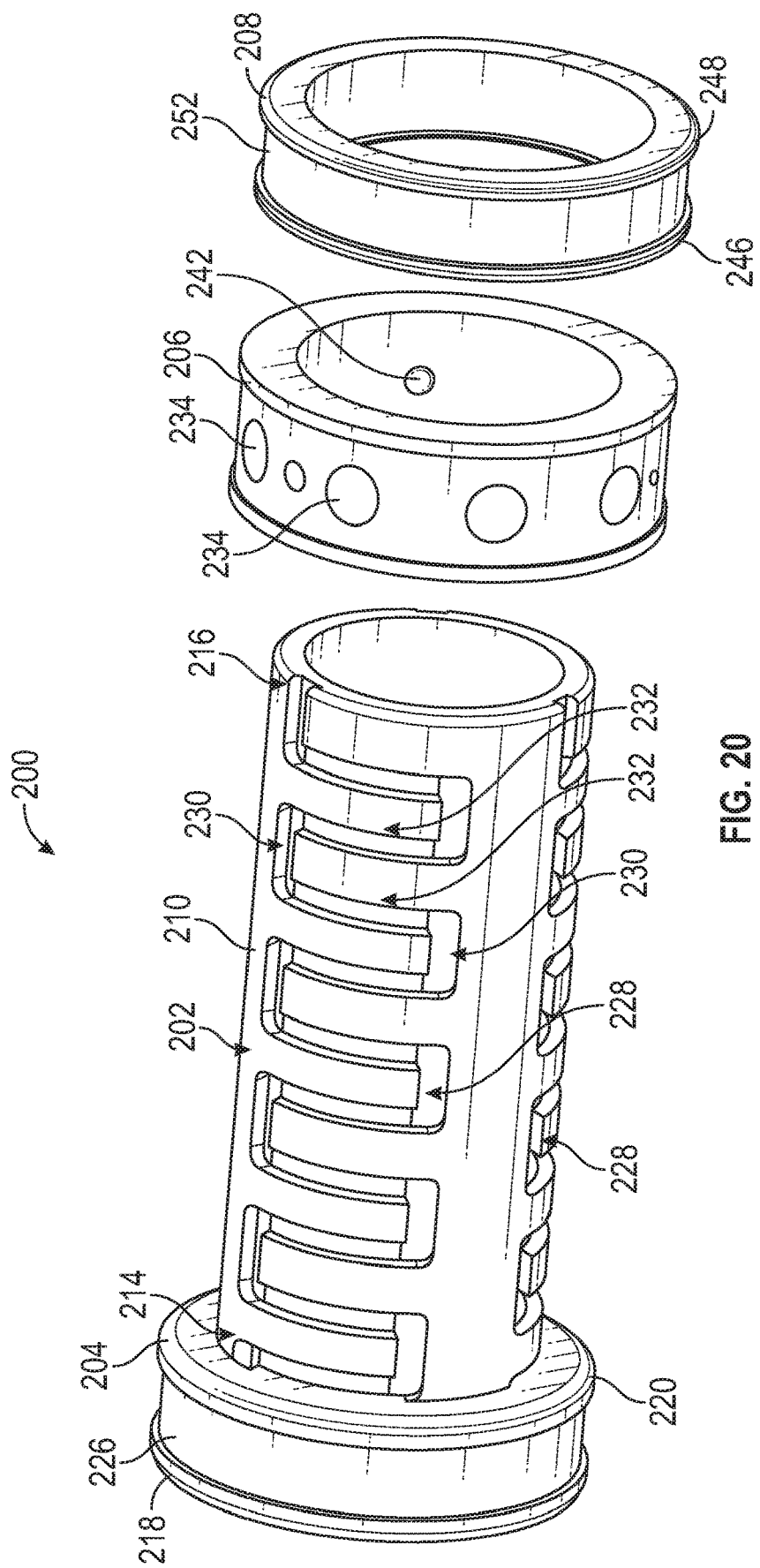
FIG. 20 is a perspective exploded view of another embodiment of a distraction device.
Figure 21:
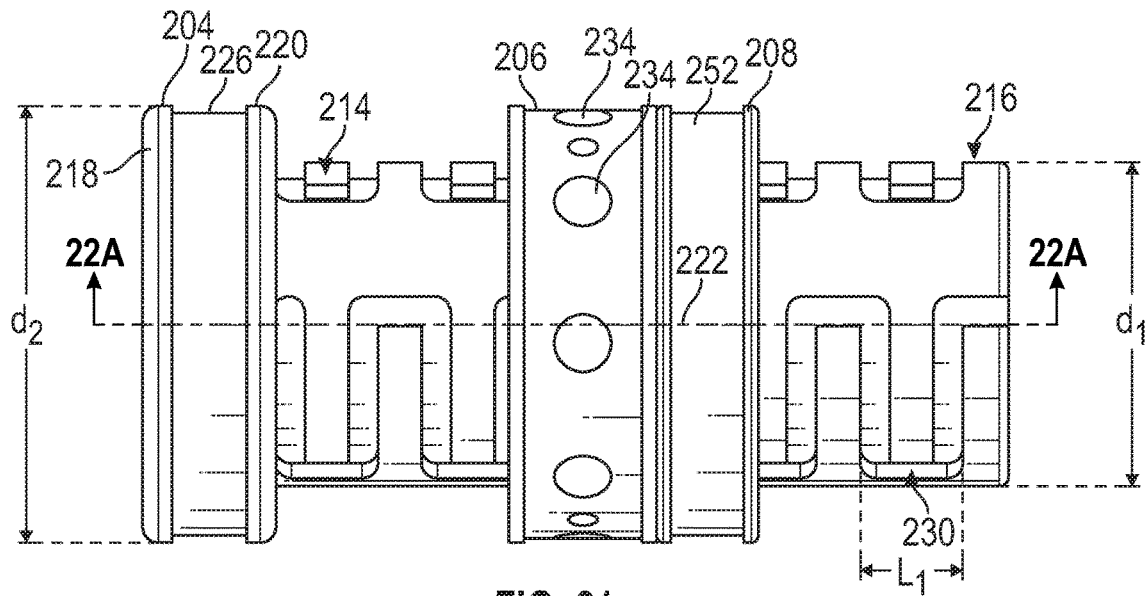
FIG. 21 is a side view of the distraction device of FIG. 20.

FIGS. 20-22B illustrate another embodiment of a distraction device 200. The distraction device 200 can include a tubular member 202 having a first attachment member 204 configured to be attached to the inner wall of a body lumen. The distraction device can further include a driver or actuator member 206 movably disposed on the tubular member 202, and a second attachment member 208 movably disposed on the tubular member 202 and configured to be attached to the inner wall of the body lumen. The tubular member 202 can comprise a main body 210 defining a lumen 212 (FIG. 22A), and having a first end portion 214 (e.g., an inflow end portion with respect to the direction of flow of intestinal contents) and a second or outflow end portion 216. In the illustrated embodiment, the first attachment member 204 is configured as a ring, collar, or flange of the tubular member 202, and is located at the first end portion 214 of the tubular member, although the member 204 may also be located at the second end portion 216. With reference to FIG. 21, the main body 210 of the tubular member 202 can have a first diameter $d_1$, and the first attachment member 204 can have a second diameter $d_2$ that is greater than the diameter $d_1$.

Figure 22A:
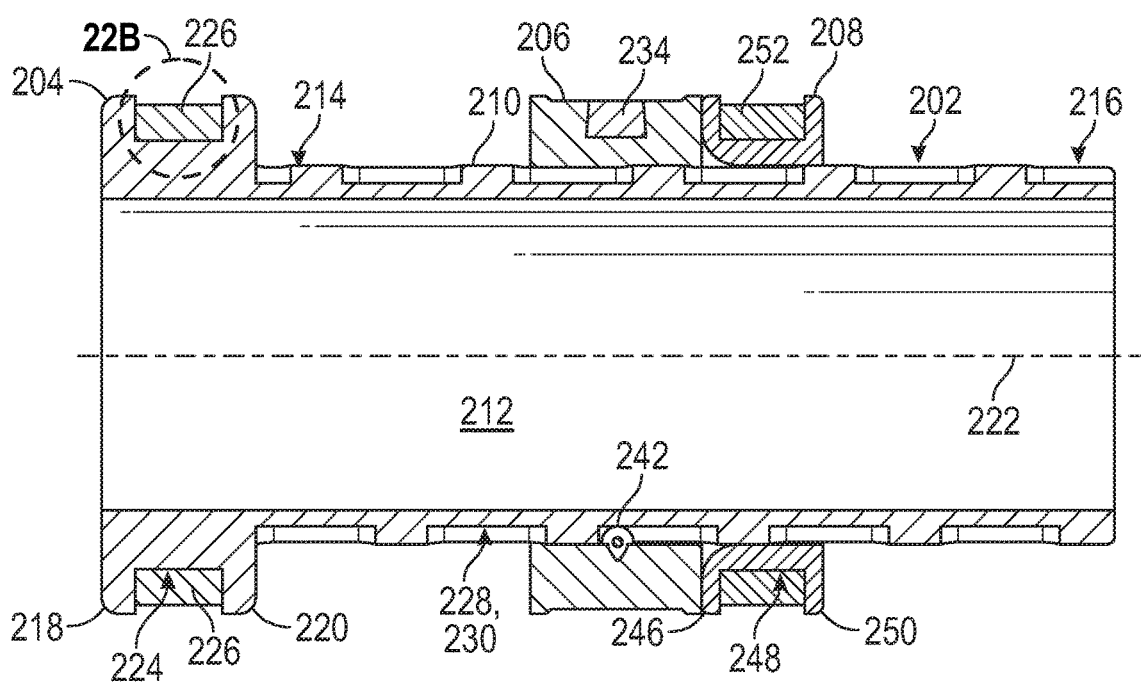
FIG. 22A is a cross-sectional side view of the distraction device of FIG. 20.

Still referring to FIG. 21, the first attachment member 204 can include two circular rim portions 218 and 220 longitudinally spaced apart from each other along an axis 222 of the tubular member 202, and defining a channel or groove 224 (FIG. 22A) therebetween. With reference to FIG. 22A, in the illustrated embodiment the first attachment member 204 is integrally-formed with the main body 210 of the tubular member 202. As used herein, the term "integrally-formed" refers to a construction that does not include any stitches, sutures, welds or bonds, fasteners, or other means for securing separately formed pieces of material to each other. However, in other embodiments the attachment member 204 may be separately formed and coupled to the tubular member 202, depending upon the particular characteristics desired.

Figure 22B:
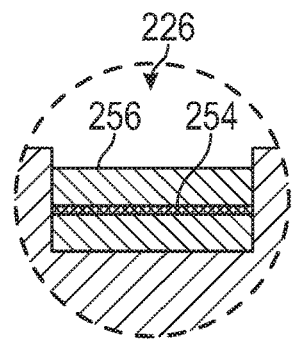
FIG. 22B is a magnified cross-sectional view of the portion of the first attachment member of the distraction device indicated in FIG. 22A.

The channel 224 can comprise a soft, flexible suture retention member 226 extending around the circumference of the attachment member 204 within the channel 224. With reference to FIG. 22B, in certain embodiments the suture retention member 226 can comprise a suture-retention layer 254 embedded within a soft encapsulating layer 256. In particular embodiments, the suture-retention layer 254 can comprise a braided layer or mesh formed from a plurality of polymer (e.g., polyester) or metal filaments (e.g., stainless steel or other biocompatible metals) configured to impart strength and suture retention properties to the member 226. The encapsulating layer 256 can comprise any of a variety of resilient natural or polymeric materials, such as silicone or any various thermoplastic elastomers.

The main body 210 of the tubular member 202 can comprise one or more guides configured as grooves or channels 228 extending along the length of the main body 210. In the embodiment of FIG. 20, the tubular member 202 includes three sets of channels 228 angularly spaced from each other around the circumference of the tubular member, although in particular embodiments the tubular member may have more or fewer sets of channels. In FIG. 20, the channels 228 can include longitudinally-extending portions 230 and circumferentially-extending portions 232. The longitudinally-extending portions 230 can be circumferentially spaced apart from each other along the surface of the main body 210 and interconnected by the circumferentially-extending portions 232 so that the portions 230 and 232 define a continuous path from the first end portion 214 to the second end portion 216 that has the shape of a square wave. The longitudinally-extending portions 230 can have a length $L_1$, and the circumferential portions 232 can have an arc length L2 (FIG. 27A) corresponding to an angular distance of 80°. In certain embodiments, the length $L_1$ can be 1 mm to 20 mm, 1 mm, to 10 mm, 1 mm to 8 mm, or 1 mm to 5 mm. In particular embodiments, the length $L_1$ can be 5 mm, although the length may be longer or shorter depending upon factors such as the particular body lumen into which the device is implanted, the size, age, sex, and/or species of the intended recipient, etc. In the illustrated embodiment, each of the longitudinally-extending portions 230 can have the same length $L_1$, although in other embodiments the lengths of the portions 230 can vary along the tubular member 202.

In the illustrated embodiment, the channels 228 are open at the second end portion 216. In other words, the final longitudinally-extending portions 232 of the respective channels 228 at the second end portion 216 are not closed or blocked, although in other embodiments the channels may be closed at the second end, as desired. For example, an annular member or ring with raised edge portions or protrusions corresponding to the channels 228 may be secured or hooked to the second end portion of the device to close the channels 228, and/or to maintain the device as an assembled unit at the completion of the distraction procedure. The ends of the channels 228 may also comprise pins or protrusions that can be screwed, welded, or adhered with glue or cement to the tubular member 202.

Figure 23:
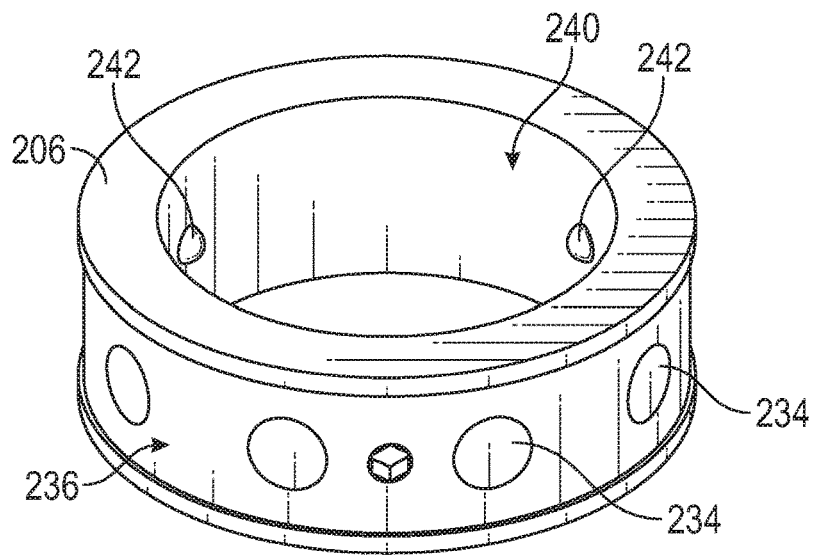
FIG. 23 is a perspective of an actuator member, according to one embodiment.
Figure 24:
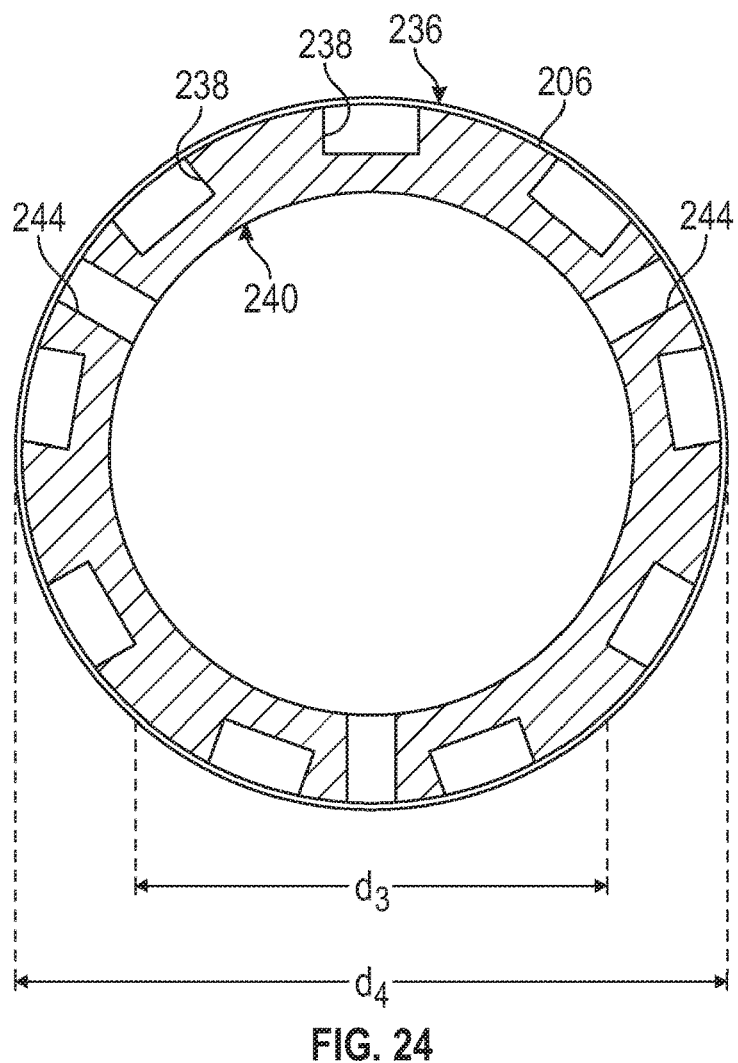
FIG. 24 is a cross-sectional end view of the actuator member of FIG. 23.
Figure 25:
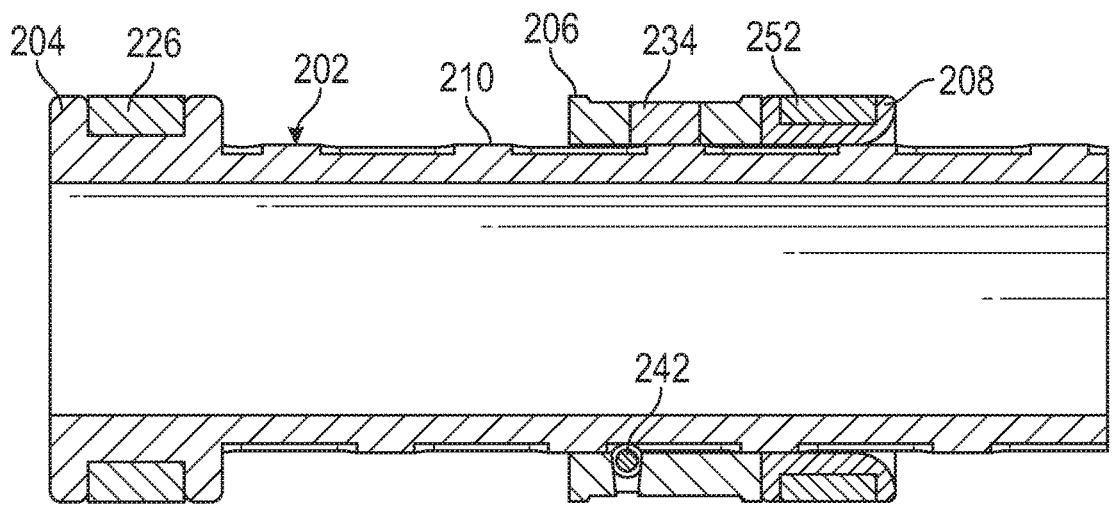
FIG. 25 is a cross-sectional side view of another embodiment of an actuator member disposed on a distraction device in which the magnets of the actuator member extend between inner and outer surfaces of the actuator member.

FIGS. 23 and 24 illustrate the actuator member 206 in greater detail. The actuator member 206 can comprise an annular body configured as a ring or collar. The actuator member 206 can have an inner diameter $d_3$ corresponding (e.g., equal to, or approximately equal to) the diameter $d_1$ of the main body 210 of the tubular member 202 to allow the actuator member 206 to slide over the main body 210. In the illustrated embodiment, the outer diameter $d_4$ of the actuator member 206 can be the same or nearly the same as the diameter $d_2$ of the first attachment member 204. The actuator member 206 can comprise a plurality of magnets 234 arrayed circumferentially along an outer surface 236 of the actuator member. The magnets 234 can be arranged in alternating polarity, or with the north poles or the south poles oriented outward. With reference to FIG. 24, the actuator member 206 can comprise a plurality of openings 238 defined in the outer surface 236 and configured to receive the magnets 234. In the illustrated embodiment, the actuator member 206 is thicker than the magnets 234, and the openings 238 do not extend through the entire thickness of the actuator member 206. As a result, the magnets 234 are not exposed through the inner surface 240 of the actuator member 206. However, in other embodiments, such as illustrated in FIG. 25, the actuator member 206 may have the same or approximately the same thickness as the magnets 234, depending upon the particular diameter profile desired. In the embodiment shown in FIGS. 23 and 24, the actuator member 206 includes nine magnets 234 angularly spaced around the circumference of the actuator member at intervals of 40°, although the actuator member may include any number of magnets having any angular spacing.

The actuator member 206 can also include one or more engagement members 242. The engagement members 242 can be configured as rods, balls, or spheres, and can at least partially protrude or extend inwardly from the inner surface 240 of the actuator member 206 by a distance sufficient to engage a corresponding channel 228 on the tubular member 202. The engagement members 242 may also be biased to an outward position by springs. In the illustrated embodiment, the actuator member 206 includes three engagement members 242 having an angular spacing corresponding to the three channels 228 of the tubular member 202 illustrated in FIG. 20 (e.g., an angular spacing of 120°). With reference to FIG. 24, the engagement members 242 can be received in corresponding openings 244 defined in the actuator member 206 and extending through the thickness of the actuator member from the outer surface 236 to the inner surface 240. When the actuator member 206 is received on the tubular member 202, the engagement members 242 can be received in the respective channels 228 such that movement of the actuator member 206 along the tubular member 202 is limited to the path defined by the channels 228, as described in greater detail below.

Figure 26:
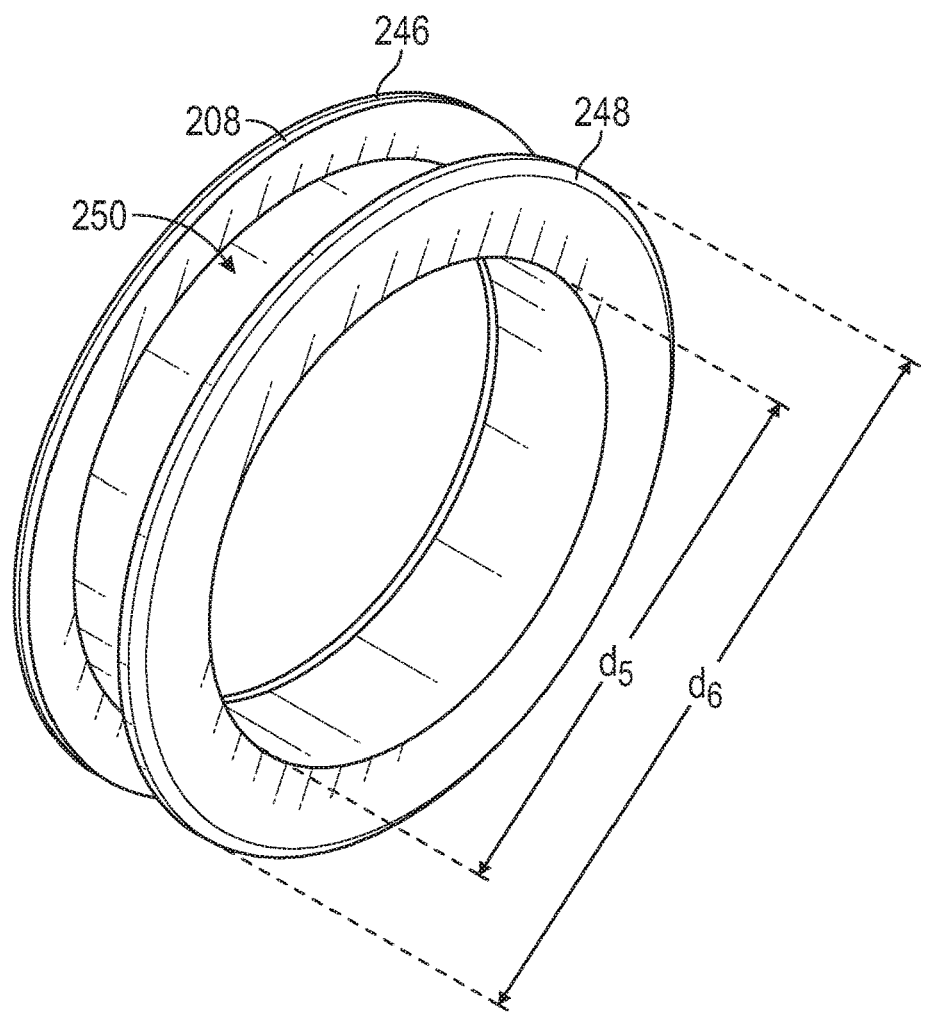
FIG. 26 is a perspective view of the second attachment member of the distraction device of FIG. 20.

FIG. 26 illustrates a representative embodiment of the second attachment member 208 in greater detail. The second attachment member 208 can be configured as a ring or collar, and can have an inner diameter $d_5$ that is the same, or nearly the same, as the diameter $d_1$ of the main portion 210 of the tubular member 202 such that the member 208 can be situated on and slide along the tubular member 202, as illustrated in FIGS. 21 and 22A. An outer diameter $d_6$ of the attachment member 208 can be the same, or nearly the same as the diameter $d_2$ of the first attachment member 204 and the diameter $d_4$ of the actuator member 206. The second attachment member 208 can include first and second rim portions 246 and 248, which can define a groove or channel 250 therebetween. Referring to FIG. 22A, the second attachment member 208 can include an annular suture retention member 252 situated in the groove 248, similar to the first attachment member 204. In certain embodiments, the suture retention member 252 can include the suture-retention and encapsulating layers described above with respect to the suture-retention member 226 and shown in FIG. 22B.

Figure 27A:
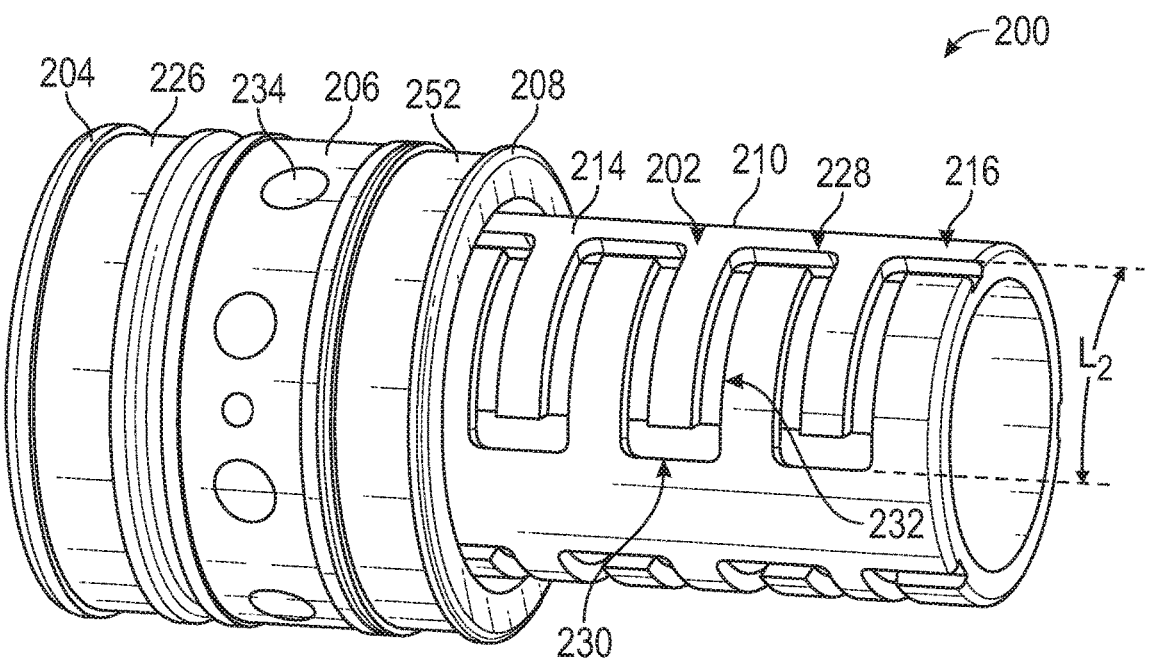
FIG. 27A is a perspective view of the distraction device of FIG. 20 with the actuator member and the second attachment member at a first position along the tubular member.
Figure 27B:
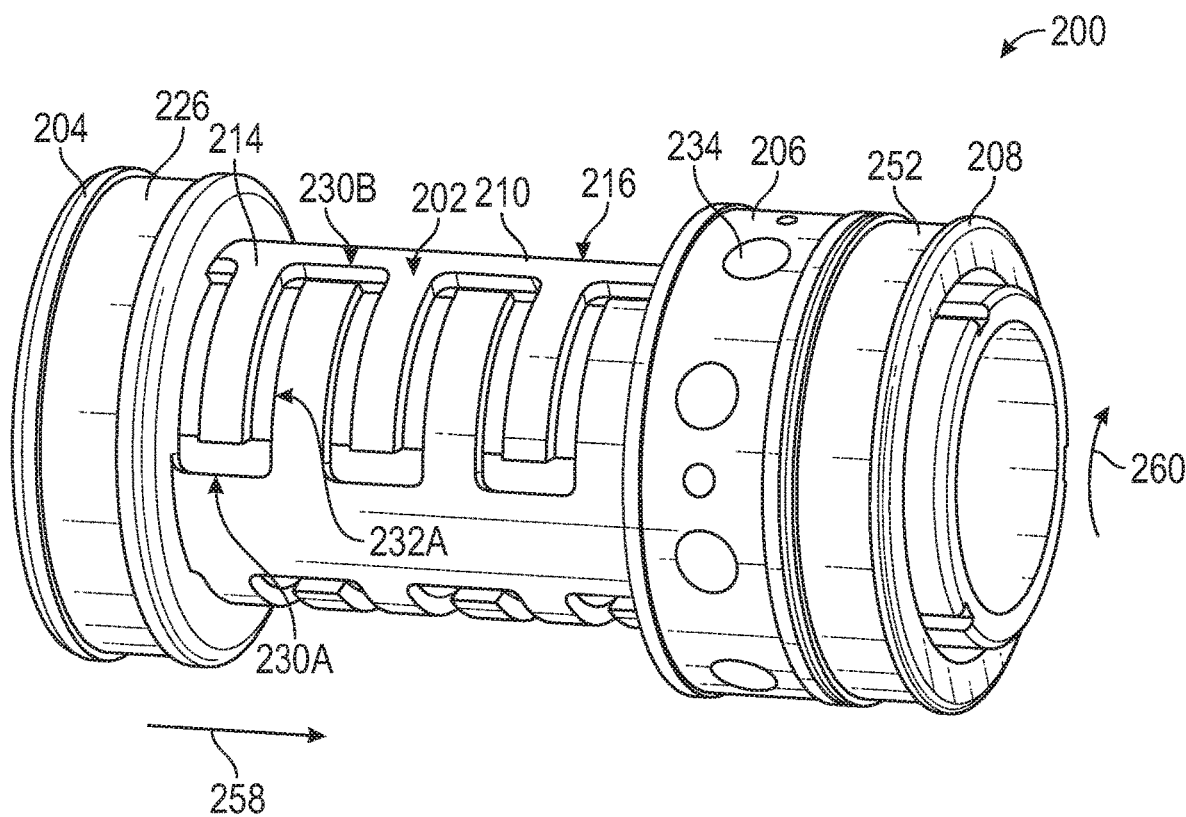
FIG. 27B is a perspective view of the distraction device of FIG. 20 with the actuator member and the second attachment member at a second position along the tubular member.

Referring to FIGS. 27A and 27B, the actuator member 206 and the second attachment member 208 can be assembled on the tubular member 202, and can be movable along the length of the tubular member 202 from a first position (FIG. 27A) to a second position (FIG. 27B). In the first position, the actuator member 206 is positioned adjacent the first attachment member 204, and the second attachment member 208 is positioned adjacent and abutting or engaging the actuator member 206 on the opposite side of the actuator member from the first attachment member 204. By moving (e.g., translating) the actuator member 206 axially along the longitudinally-extending portions 230 of the channels 228, and rotating the actuator member 206 along the circumferentially-extending portions 232 of the channels 228, the actuator member 206 can be advanced axially along the length of the tubular member 202 from the first position to the second position along the channels 228. Because the leading surface of the actuator member 206 engages the second attachment member 208, and is rotatable relative to the attachment member 208, longitudinal motion of the actuator member 206 causes corresponding longitudinal motion of the second attachment member 208 along the tubular member 202 without rotating the attachment member 208.

For example, with reference to FIG. 27B, to advance the actuator member 206 and the second attachment member 208 toward the second position from the first position, the actuator member 206 can first be moved axially along the axially-extending channel portions 230A in the direction indicated by arrow 258. When the engagement members 242 reach the end of the channel portions 232A, the actuator member can be rotated in the direction indicated by arrow 260 (e.g., clockwise when viewed from the second end portion 216) such that the engagement members 242 (FIG. 22A) travel along the respective circumferentially-extending portions 232A of the channels 228. At the completion of the rotation, the engagement members 242 are located at the ends of the channel portions 232A, and the actuator member 206 and the second attachment member 208 have traveled axially along the tubular member 202 by a distance equal to the length $L_1$ (FIG. 21) of the channel portions 230A. To produce further axial motion of the actuator member 206 and the attachment member 208, the actuator member 206 can be moved axially along the axially-extending channel portions 230B, and rotated in the opposite direction (e.g., counterclockwise when viewed from the second end portion 216). The actuator member 206 can be used to advance the second end portion 208 along the entire length of the tubular member 202 in this fashion. In some embodiments, a spring can be disposed on or around the main body 210 of the tubular member 202 and configured to facilitate movement of the actuator member 206, and/or to maintain tension on the tissue stretched between the attachment members.

Figure 28:
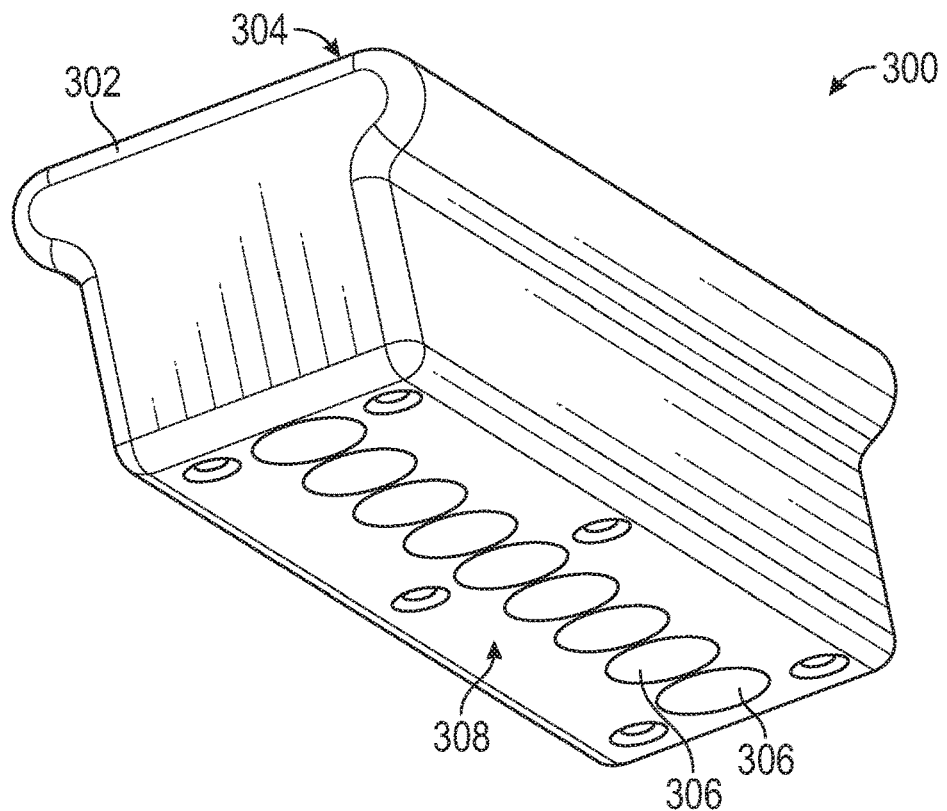
FIG. 28 is a perspective view of a control device, according to one embodiment.
Figure 29:
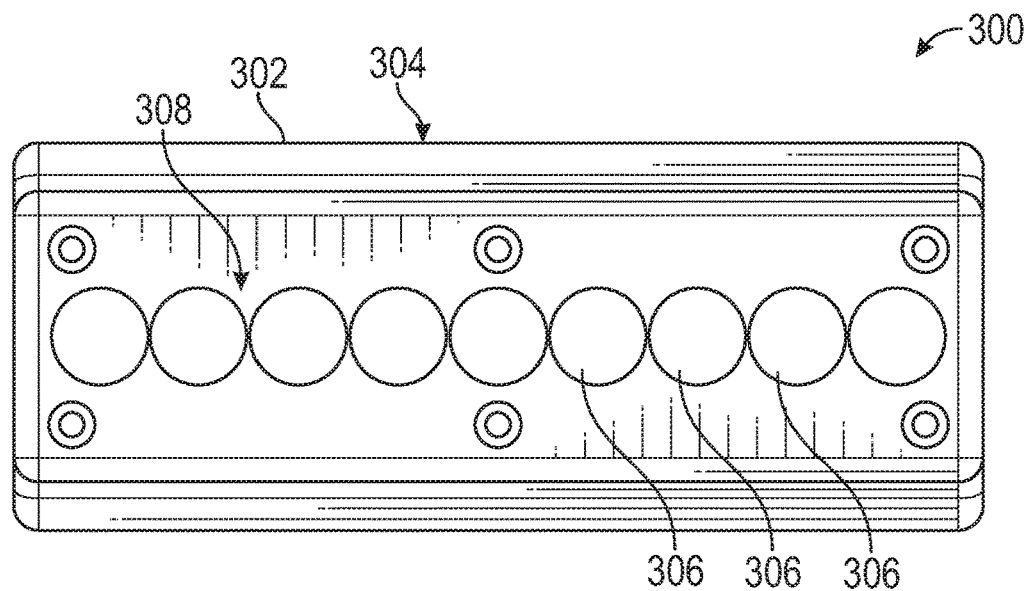
FIG. 29 is a bottom plan view of the control device of FIG. 28.

FIGS. 28 and 29 illustrate an embodiment of a magnetic control device 300 which can be used to effect the motion of the actuator member 206 and the second attachment member 208 of the distraction device 200 described above. The control device 300 can comprise a main body 302 including a handle portion 304. The main body 302 can comprise a plurality magnets 306 arrayed in a linear fashion along a length of a lower surface 308 of the main body 302. In the illustrated embodiment, the magnets 306 are lined up edge-to-edge with each other, but may also be spaced apart by any suitable spacing, as desired. In certain embodiments, the magnets 306 can be permanent magnets such as rare-earth magnets (e.g., comprising rare earth metals such as neodymium). In other embodiments, one or more of the magnets 306 can be electromagnets so that the magnetic fields of the magnets can be selectively strengthened or weakened by application of an electric current. In certain embodiments, the magnets 306 can be arranged in alternating polarity, or may be arranged with their north poles facing outward or the south poles facing outward. In the illustrated embodiment, the controller 300 comprises nine magnets 306 similar to the distraction device 200, although the controller may comprise any number of magnets 306.

In certain embodiments, the tubular member 202, the actuator member 206, and/or the second attachment member 208 can be made from biocompatible polymeric materials, such as polyetheretherketone (PEEK), polytetrafluoroethylene (PTFE), acetal (e.g., polyoxymethylene), polyesters including polycaprolactone, etc. In other embodiments, one or more of the components above can be made from biocompatible metals, such as stainless steel, cobalt chromium, etc. In certain embodiments, the tubular member 202, the actuator member 206, and/or the second attachment member 208 can comprise a biodegradable material (e.g., polycaprolactone) configured such that the device 200 can slowly break down over time, and any non-biodegradable components (e.g., the magnets 234) can pass naturally through the bowel and do not need to be surgically retrieved.

In certain embodiments, the distraction device 200 and/or the control device 300 can comprise one or more sensors configured to allow the user to determine the axial position and/or the angular position of the actuator member 206 and/or of the second attachment member 208 relative to the tubular member 202. For example, the tubular member 202 and/or the control device 300 can comprise a plurality of proximity sensors, such as Hall-effect sensors, arrayed along the tubular member 202 and/or circumferentially around the tubular member 202, which can interact with the magnets 234 to produce signals indicative of the angular and/or axial position of the actuator member 206 relative to the tubular member 202. In certain embodiments, the distraction device 200 can include a controller, such as a programmable logic controller or an application-specifc integrated circuit (ASIC), including a radio transmitter to transmit information of the angular and/or axial position of the actuator member 206 to the control device 300. This information can be utilized to determine the sequence of motions of the control device 300 to effect motion of the actuator member 206 along the channels 228 after implantation of the device 200 in a patient, as described in greater detail below. The control device 300 can also include one or more of visual, audible, and/or tactile feedback mechanisms such as LEDs, speakers, vibrator motors, etc., that can be activated, for example, to indicate to a user that the control device and/or the actuator member 206 are appropriately positioned to begin an increment of axial displacement of the actuator member.

Figure 30:
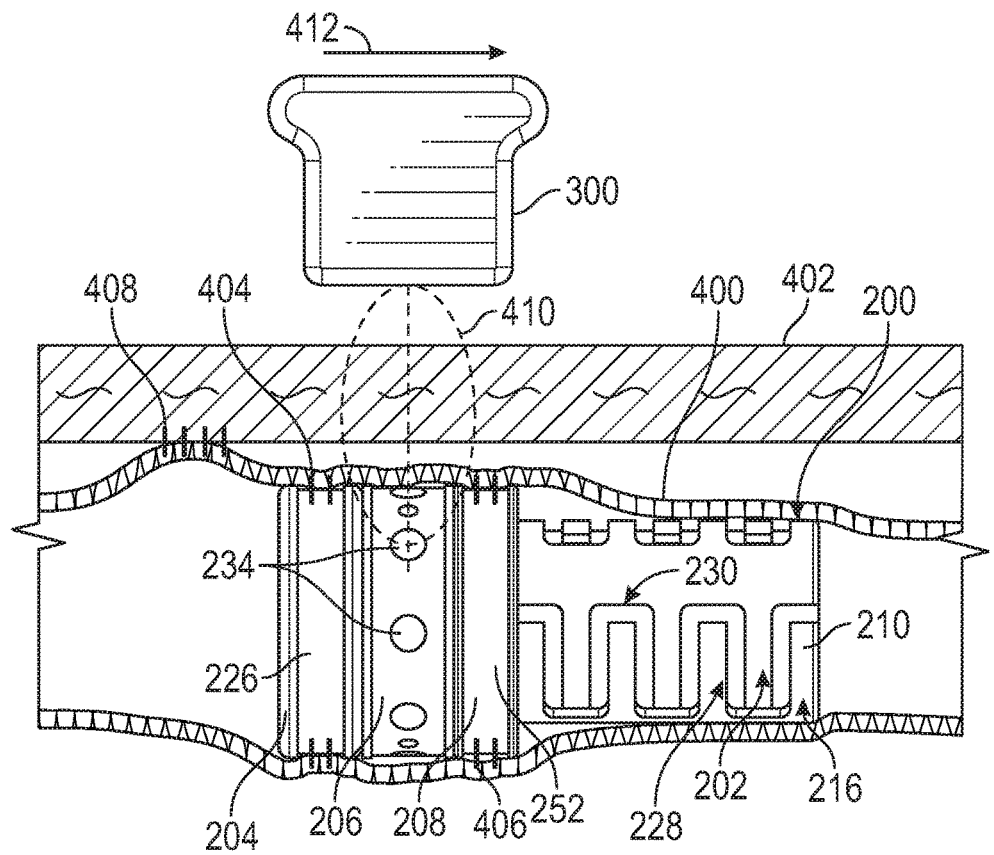
FIG. 30 is a cross-sectional view illustrating the distraction device of FIG. 20 implanted in the lumen of the small intestine with the actuator member and the second attachment member in the first position and interacting with a magnetic field of the control device of FIG. 28 applied from outside the body.

The distraction device 200 may be implanted in an open surgical procedure, but may also be implanted endoscopically or laparoscopically. FIG. 30 illustrates the distraction device 200 implanted in a bowel 400 after, for example, a bowel resection procedure. The actuator member 206 and the second attachment member 208 are shown disposed at the first end portion 214 of the tubular member 202. The first and second attachment members 204 and 208 can be sutured to the bowel wall by suturing through the respective suture retention members 226 and 252. For example, sutures 404 can connect the first attachment member 204 to the bowel 400 around the circumference of the attachment member 204, or any portion thereof, and sutures 406 can connect the second attachment member 208 to the bowel 400 around the circumference of the attachment member 208, or any portion thereof. In certain embodiments, the diameters of the first attachment member 204, the actuator member 206, and/or the second attachment member 208 can be greater than the natural diameter of the bowel 400 to aid, for example, in forming a seal with the bowel walls and directing bowel contents through the tubular member 202. The diameters of the components may also be sized to promote an increased diameter of the bowel upon completion of the distraction procedure.

In the case of a bowel resection, after excision of the diseased bowel, the remaining portions of the intestine 400 can be anastomosed with the distraction device 200 located upstream (with respect to the direction of flow of bowel contents), downstream, or extending across the anastomosis depending upon, for example, the location of the resected portion along the length of the bowel 400, or constraints imposed by the surrounding anatomy. In certain embodiments, the bowel 400 can also be surgically fixed to the abdominal wall 402 using, for example, an enteropexy technique. For example, in certain embodiments the bowel 400 can be sutured to the abdominal wall 402 with sutures generally indicated at 408. The enteropexy can be adjacent the first attachment portion 204 of the distraction device 200 (e.g., upstream of the first attachment portion 204), and can serve to prevent longitudinal motion of the bowel 400 with respect to the abdominal wall 402, and/or rotation of the bowel with respect to the abdominal wall, during subsequent distraction procedures.

Figure 31:
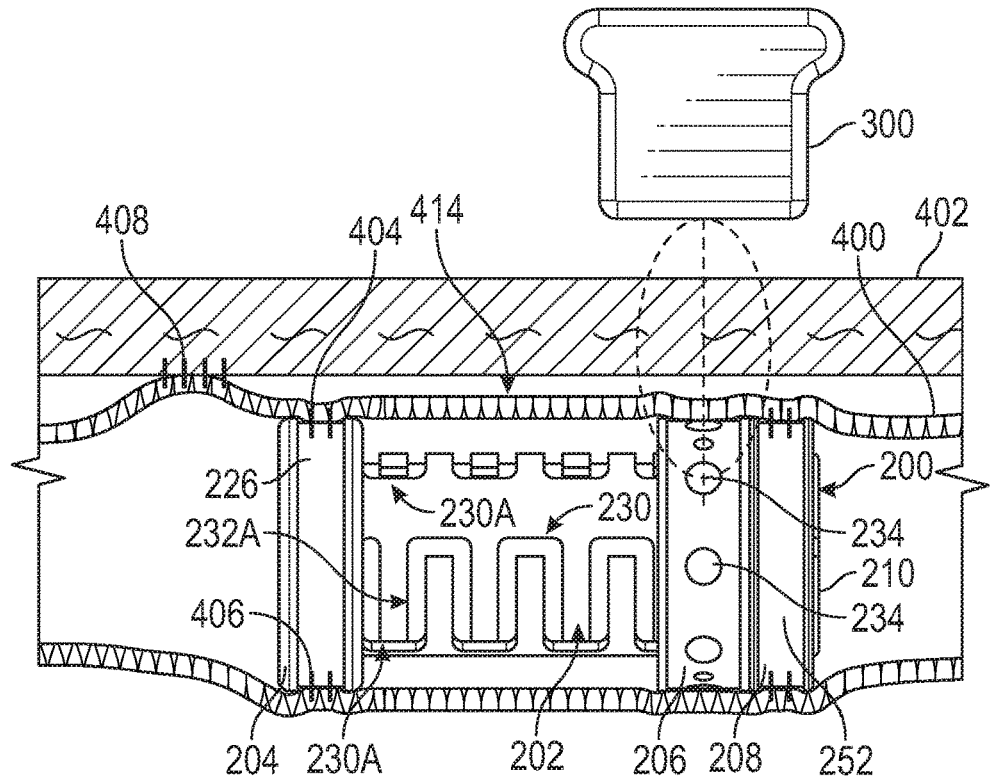
FIG. 31 is a cross-sectional view illustrating the distraction device of FIG. 20 implanted in the lumen of the small intestine with the actuator member and the second attachment member at the second position.

Still referring to FIG. 30, after implantation of the distraction device 200 in the patient, the control device 300 can be positioned on or near the patient's body adjacent, but spaced apart from, the implanted distraction device 200, external to the abdominal wall 402. The control device 300 can be positioned with its longitudinal axis perpendicular to the longitudinal axis of the distraction device 200. One or more of the magnets 306 of the control device 300 can magnetically couple with one or more magnets 234 of the actuator member 206 (e.g., the magnets 234 closest to the abdominal wall 402) from outside the patient's body (note magnetic field lines generally indicated at 410). The control device 300 can then be advanced axially along the tubular member 202 in the direction of arrow 412 toward the second end portion 216 by a distance equal to the length of the channel portions 230A (FIG. 31). Due to the magnetic interaction between the magnets 306 of the control device 300 and the magnets 234 of the actuator member 206, this can cause the actuator member 206 to move axially along the channel portions 230A and push the second attachment member 208 along the tubular member 202 toward the second end portion 216. As the second attachment member 208 moves away from the first attachment member 204, the bowel 400 can be stretched between the two attachment members.

The control device 300 can then be positioned with one end over the actuator member 206, and moved perpendicular to the axis of the distraction device (e.g., into the plane of the page in FIG. 30) such that the magnets 306 of the control member 300 pass successively over the actuator member 206. This can cause the actuator member 206 to rotate as successive magnets 306 of the control member 300 magnetically couple with corresponding magnets 234 on the actuator member 206 as it rotates, causing the engagement members 242 to move along the circumferentially-extending portions 232A of the channels 228. With the engagement members 242 of the actuator member 206 located in the circumferentially-extending portions 232A of the channels 228, mechanical engagement between the engagement members 242 and the walls of the channels 230A can prevent the actuator member 206 and the second attachment member 208 from moving upstream along the tubular member 202 back toward the starting position, even when the magnetic influence of the control device 300 is removed.

This can apply tensile force to the bowel 400, stretching the portion of the bowel between the attachment members 204 and 208 beyond its natural length to promote enterogenesis. The process above can be repeated to replicate the motion described above with respect to FIGS. 27A and 27B to achieve a desired position of the second attachment member 208 along the tubular member 202.

The position of the actuator member 206 and the second attachment member 208 can be gradually moved along the tubular member 202 with the control member 300 in increments as described above over a time interval of, for example, days, weeks, or months. With reference to FIG. 31, when the actuator member 206 and the second attachment member 208 reach the second end portion 216 of the tubular member 202, the distraction device 200 can have induced the generation of new bowel tissue 414, and increased the overall length of the bowel 400 by a distance equal to the distance of travel of the second attachment member 208 between its starting and ending points. In the example above in which the channel portions 230 are 5 mm long, this can result in the creation of about 5 cm of new bowel tissue.

In certain embodiments, when the actuator member 206 and the attachment member 208 reach the end of the channels 228, the actuator member and the attachment member can be moved axially with the control member such that they slide off of the tubular member 202. The actuator member 206 and/or the magnets 234 can then pass naturally out of the bowel with the flow of bowel contents. The sutures 404 and 406 can be configured to degrade or dissolve after a selected period of time, along with main bodies of the tubular member 202 and the second attachment member 208. Any remaining components such as the suture retention members 226 and 252 can also pass through the intestine with the natural flow of bowel contents. In this manner, a second surgical procedure to remove the device is unnecessary.

Figure 32A:
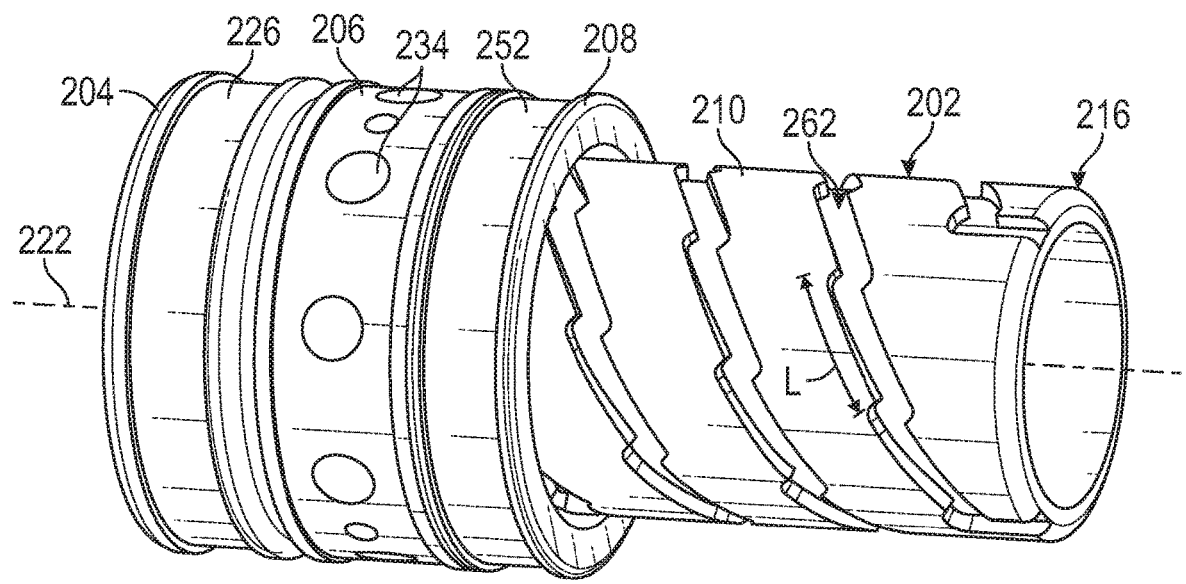
FIGS. 32A and 32B are perspective views illustrating another embodiment of a distraction device.
Figure 32B:
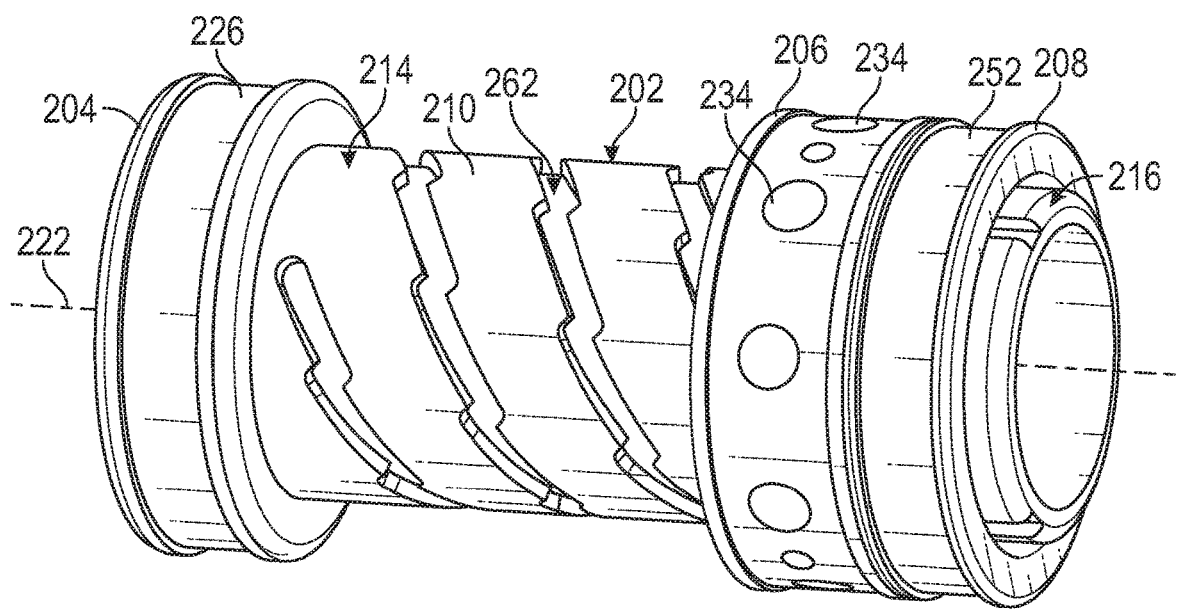
Figure 33:
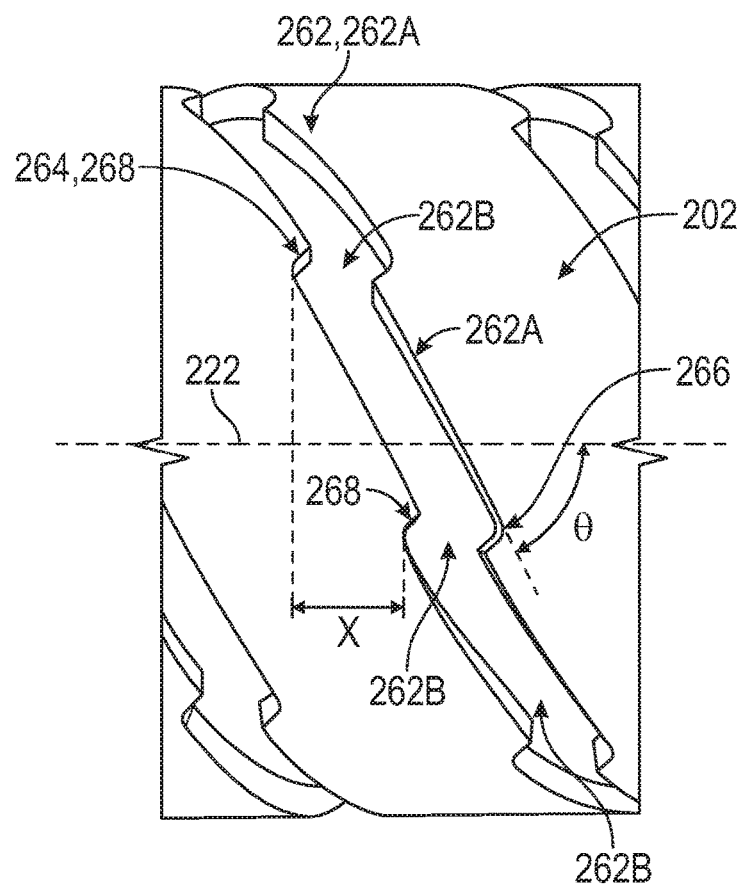
FIG. 33 is a magnified view illustrating a portion of a channel of the tubular member of the distraction device of FIGS. 32A and 32B.

FIGS. 32A, 32B, and 33 illustrate another embodiment of the distraction device 200 in which the tubular member 202 defines channels 262 extending helically around the tubular member 202. The channels 262 can comprise a series of linear channel portions or segments 262A extending along the outer surface of the tubular member 202 at an angle to the longitudinal axis 222 of the tubular member. Each of the portions 262A can have a first end portion 264 and a second end portion 266, with the first end portion 264 being closer to the first attachment member 204 than the second end portion 266. The second end portion 266 of each channel portion 262A can be offset from the first end portion 264 of the next channel portion 262A by relatively short axial channel portions 262B that extend parallel to the axis 222 of the tubular member 202. In this manner, the channel portions 262 form a zig-zag pattern, and successive channel portions 262A are interconnected by the channel portions 262B.

The first end portions 264 of the channel portions 262A also define recesses or pockets 268 offset axially toward the first end portion 214 from the second end portions 266 of the preceding channel segments 262A. For example, with reference to FIG. 33, the channel portions 262A can define an angle $\theta$ with the longitudinal axis 222 of the tubular member, and can have a length L (FIG. 32A) such that successive recessed portions 268 are offset from each other axially by a distance x. In certain embodiments, the angle $\theta$ can be from 5° to 90°, 10° to 70°, 10° to 50°, 10° to 40°, or 10° to 30°. In particular embodiments, the angle $\theta$ can be 30°. In certain embodiments, the length L can be from 1 mm to 50 mm, 1 mm to 40 mm, 1 mm to 30 mm, 1 mm to 20 mm, or 1 mm to 10 mm. In particular embodiments, the length L can be 8 mm. Accordingly, the axial offset distance x between successive recessed portions 268 can be from 1 mm to 20 mm, 1 mm to 15 mm, 1 mm to 10 mm, 2 mm to 8 mm, 3 mm, 4 mm, or 5 mm.

The engagement members 242 of the actuator member 206 can be received in the channels 262. As the actuator member 206 rotates, the actuator member 206 can be urged or guided axially along the tubular member 202 by the interaction of the engagement members 242 with the walls of the angled channel portions 262A. When the engagement members 242 reach the end of a respective channel portion 262A, the engagement members 242 can move axially along the portions 262B (e.g., back toward the first attachment member 204) and can settle into the recess 268 defined at the first end portion 264 of the next respective channel portion 262A. The walls of the recesses 268 can prevent further movement of the actuator member 206 in the axial direction toward the first attachment member 204. Thus, when implanted in a bowel, the force applied to the second attachment member 208 by the stretched bowel tissue can urge the actuator member 206 in a direction back toward the first end portion 214 such that the engagement members 242 are received or seated in the recesses 268, preventing further upstream motion of the actuator member and maintaining tension on the bowel tissue. Due to the generally helical nature of the channels 262, axial motion of the actuator member 206 and the attachment member 208 can be effected by transverse motion of the control device 300 relative to the longitudinal axis of the tubular member 202 (e.g., into the plane of the page in FIGS. 32A and 32B), causing the actuator member 206 to rotate as described above.

In other embodiments, the location of the channels and the engagement members can be reversed. For example, the tubular member 202 can comprise ridges, while the actuator member 206 comprises channels configured to engage and follow the path defined by the ridges on the tubular member. The channels may also comprise other shapes, such as smooth helices, sinusoidal wave patterns, axially-extending main channels with a plurality of longitudinally spaced-apart, circumferentially-extending recesses or detents, etc. In yet other embodiments, the first attachment member 204, the actuator member 206, and/or the second attachment member 208 can comprise sealing members configured to form a seal with the bowel wall and help prevent leakage of bowel contents around the members.

Figure 34:
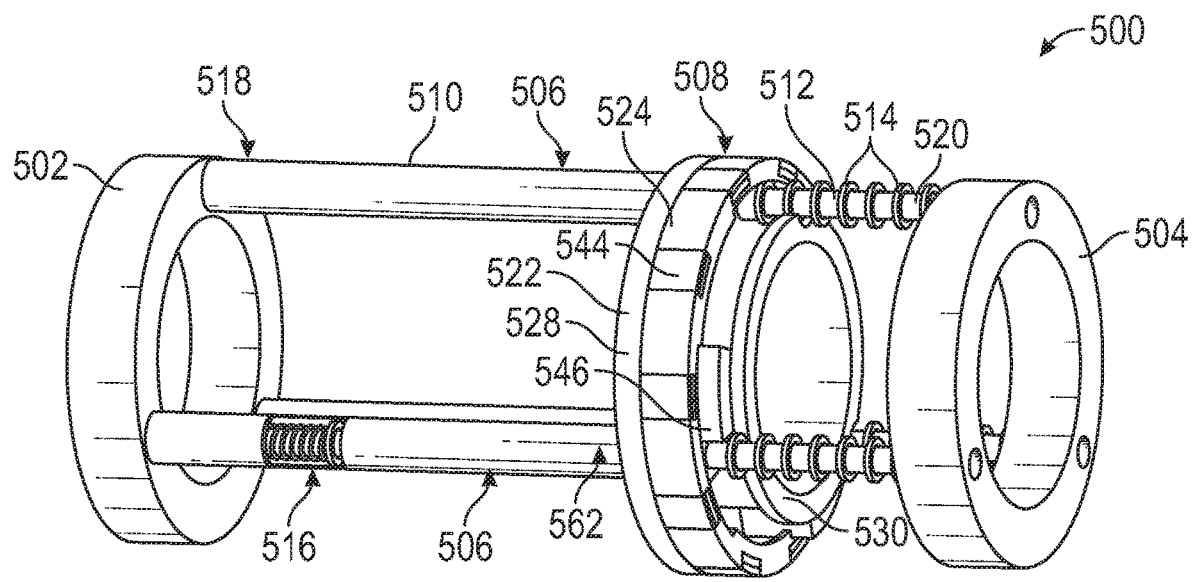
FIG. 34 is a perspective view of another embodiment of a distraction device.

FIG. 34 illustrates another embodiment of a distraction device 500 that can be configured for implantation within a body lumen, or secured extraluminally around the exterior of a tubular organ, such as the large or small intestine. The distraction device 500 can include a first attachment member 502 and a second attachment member 504 interconnected by a plurality of tubular extension members 506 (three in the illustrated embodiment). An actuator assembly 508 can be coupled to the extension members 506 and positioned between the first attachment member 502 and the second attachment member 504.

The extension members 506 can include first tubular members or portions 510 and coaxial second tubular members or portions 512. The diameter of the first tubular members 510 can be sized so that the second tubular members 512 can be disposed within and movable relative to the first members 510 in a telescoping manner between a retracted position (corresponding to the initial length of the device at implantation) and an extended position (corresponding to an extended length), similar to the embodiment of FIG. 1 above. The second tubular members 512 can include a plurality of engagement members configured as collars, rings, teeth, or flanges 514 spaced apart from each other along a length of the members 512. Each of the first members 510 can include a spring 516 disposed within its lumen. When the second members 512 are in the retracted position, the second members 512 are received within the first members 510 and can compress the springs 516. In the illustrated embodiment, the first attachment member 502 is coupled to first end portions 518 of first members 510, and the second attachment member 504 is coupled to second end portions 520 of the second members 512 opposite the first attachment member. Axial motion of the second members 512 out of the first members 510 can cause corresponding axial motion of the second attachment member 504 toward or away from first attachment member 502.

The first and second attachment members 502 and 504 can be configured as rings or collars defining a central lumen extending along the length of the device, and can be configured for intraluminal or extraluminal attachment to a tubular organ. For example, in certain embodiments the first and second attachment members 502 and 504 can comprise a resilient biocompatible material such as silicone, and can include an embedded suture-retention structure or layer (e.g., metal or polyester mesh) similar to the layer 254 of FIG. 22B.

Figure 35:
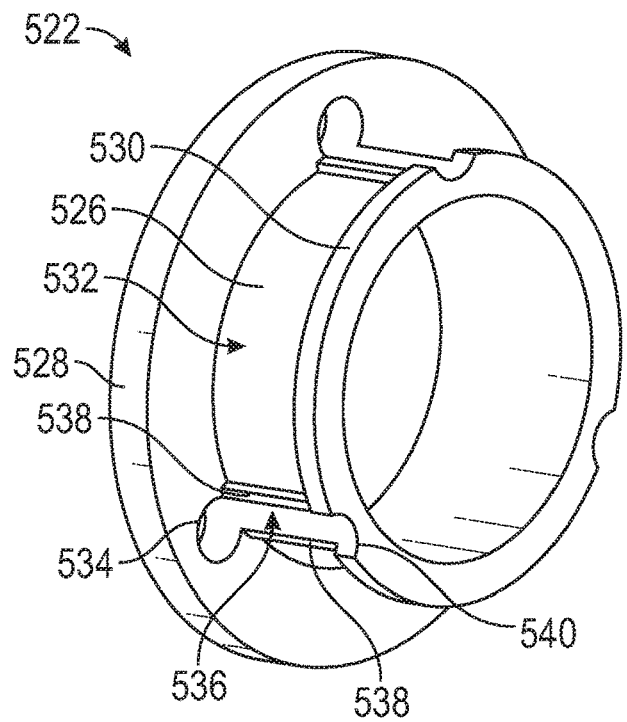
FIG. 35 is a perspective view of a support member of an actuator assembly of the distraction device of FIG. 34.

The actuator assembly 508 can comprise a first member configured as a support member 522, and a second member configured as an actuator member 524. With reference to FIG. 35, the support member 522 can configured as a collar or ring comprising a tubular body 526, and having a first annular flange portion 528 and a second annular flange portion 530 at the opposite end of the tubular body from the first flange 528. The first and second flanges 528 and 530 can define a channel 532 extending circumferentially around the tubular body 526 and configured to receive the actuator member 524, as described in further detail below. The first flange 528 can define a plurality of circumferentially spaced-apart openings 534. The openings 534 can be in communication with axially-extending channels or recesses 536 defined in the surface of the tubular body 526. The channels 536 can be bounded on either side by ridges, rims, or lips 538. The radially outward surface of the second flange 530 can define corresponding rounded recesses 540.

Figure 36:
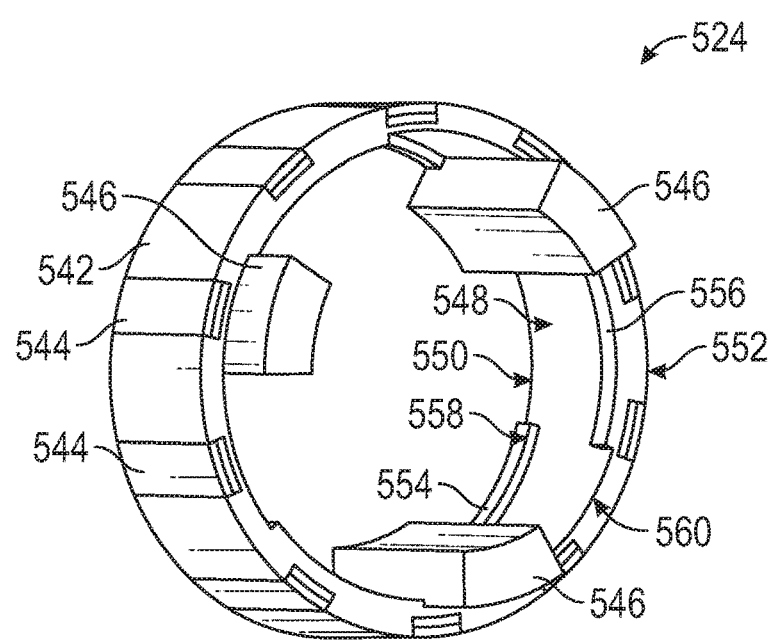
FIG. 36 is a perspective view of an actuator member of the actuator assembly of the device of FIG. 34.

With reference to FIG. 36, the actuator member 524 can be configured as a collar or ring including an annular main body 542, and including a plurality of magnets 544 arrayed circumferentially around the outer surface of the main body 542. The magnets 544 may be arranged in alternating north/south polarity around the circumference of the actuator member 524, or with all of the magnets 544 having the same pole oriented outward. The actuator member 524 can further comprise a plurality of guide members 546 coupled to and arrayed circumferentially around the inside surface 548 of the actuator member. The inside surface 548 can comprise a first edge portion 550 and a second edge portion 552 axially offset from the first edge portion. The first edge portion 550 can define a plurality of first ridges, rims, or lips 554 extending radially inwardly and circumferentially along the first edge portion 550. The second edge portion 552 can comprise a plurality of second ridges, rims, or lips 556 extending radially inwardly and circumferentially along the first edge portion 552.

In the illustrated embodiment, second ridges 556 are axially offset from the first ridges 554 along the width of the actuator member 524, and radially offset from the first ridges 554 around the circumference of the actuator member. For example, the first ridges 554 can extend from respective guide members 546 in a first radial direction (e.g., counterclockwise in FIG. 36), and the second ridges 556 can extend the guide members 546 in the opposite radial direction (e.g., clockwise in FIG. 36). In the illustrated embodiment, the first and second ridges 554 and 556 can have similar lengths. Thus, end portions 558 of the first ridges 554 can be located at the same radial position along the circumference of the actuator member 524 as end portions 560 of the corresponding second ridges 556. In some embodiments, the end portions 558 of the first ridges 554 may overlap with the end portions 560 of the second ridges 556.

Referring again to FIG. 34, when the actuator assembly 508 is assembled on the distraction device 500, the support member 522 can be coupled to second end portions 562 of the first tubular members 510 opposite the first attachment member 502. The second tubular members 512 can extend through the openings 534 in the flange 528 (FIG. 35) of the support member 522, through the channels 536, and through the recesses 540 in the flange 530. The guide members 546 of the actuator member 524 can be received in the channel 532 of the support member 522. The actuator member 524 can be rotatable relative to the support member 522 such that the guide members 546 move or slide in the channel 532 between limits of motion established by the ridges 538 (FIG. 35). The first and second flanges 528 and 530 can prevent axial motion of the guide members 546 and, hence, of the actuator member 524, relative to the support member 522.

Figure 37:
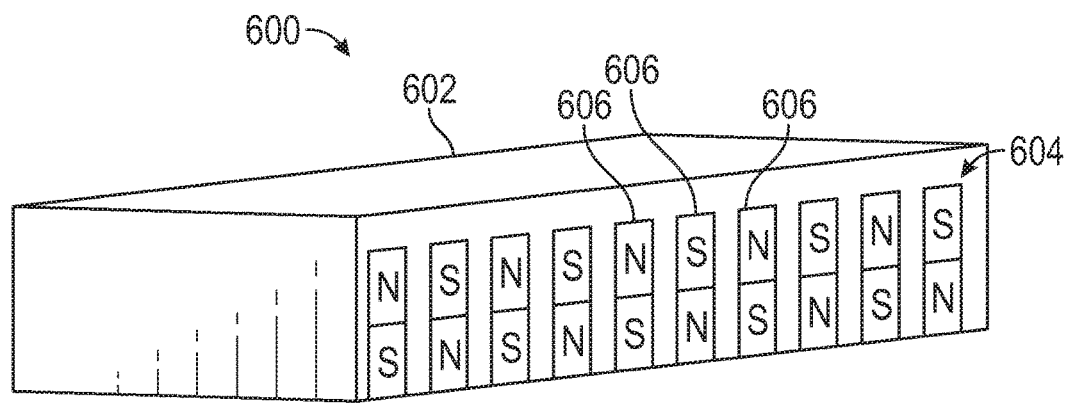
FIG. 37 is a perspective view of a representative embodiment of a control device that can be used with the distraction device of FIG. 34.

FIG. 37 illustrates another embodiment of a control device 600 that may be used with the distraction device 500, and/or with any of the other distraction device embodiments described herein. The control device 600 can comprise a main body 602 including a surface 604 in which are disposed a plurality of magnets 606. The magnets 606 can be arranged with their north and south poles alternatingly oriented toward one edge or the other edge of the surface 604.

In use, the distraction device 500 may be implanted within the lumen of an organ such as the large or small intestine, as described above. When implanted intraluminally, the attachment members 502 and 504 can be sutured to the interior of the intestine. In other embodiments, the device 500 may also be deployed extraluminally around the exterior of the intestine such that the organ extends through the openings defined by the attachment members 502, 504, through the support member 522, and such that the extension members 506 are arrayed around the outside of the intestine. The attachment members 502 and 504 can then be sutured to the exterior of the intestine to hold the device in place.

In either intraluminal or extraluminal use, the first and second attachment members 502 and 504 can be sutured to the bowel with the extension members 506 in the initial configuration, and with the springs 516 compressed inside the first members 510. The bowel can be fixed to the interior side of the anterior abdominal wall, and a suture mark can be used to indicate the location of the actuator assembly 508 for aligning the control device 600. In an initial state or first position, the actuator member 524 can be positioned relative to the support member 522 such that the ridges 558 (FIG. 36) engage the flanges 514 (FIG. 43) of the second members 512 that are located at the openings of the tubular members 510 (e.g., upstream of the actuator member 524 relative to the direction of flow of bowel contents). To increase the distance between the attachment members 502, 504 and apply force to the bowel, the control device 600 can be positioned with the surface 604 located over the actuator member 524, and moved perpendicular to the axis of the distraction device in a first direction (e.g., to the right when viewed from the end of the second attachment member 504) such that the magnets 606 of the control device 600 pass successively over the actuator member 524 and cause the actuator member 524 to rotate in a first direction (e.g., clockwise when viewed from the end of the second attachment member 504) toward a second position.

As the actuator member 524 rotates, the first ridges 554 can be rotated past and out of the way of the flanges 514 of the second tubular members 512 so as to unblock the flanges 514. Once the flanges 514 are unblocked, the second tubular members 512 can advance axially relative to the first tubular members 510 under the influence of the springs 516 until the flanges 514 contact the second ridges 556, which have moved into the path of the flanges 514 by rotation of the actuator member 524. Thus, the second ridges 556 can stop further axial movement of the second tubular members 512. The control device 600 can then be moved in a second direction opposite the first direction and perpendicular to the axis of the device 500 to rotate the actuator member 524 back to the first position wherein the first ridges 554 contact the next set of flanges 514 and block further axial movement of the second tubular members 512. In this manner, the axial distance between the first and second attachment members 502 and 504 can be increased in increments corresponding to the distance between the flanges 514 of the tubular members 512.

In certain embodiments, any of the components of the device 500 can comprise biodegradable materials as described above such that the device can naturally break down over a selected period of time, and can pass naturally from the bowel after the distraction procedure without requiring a second surgery to retrieve the device.

Figure 38:
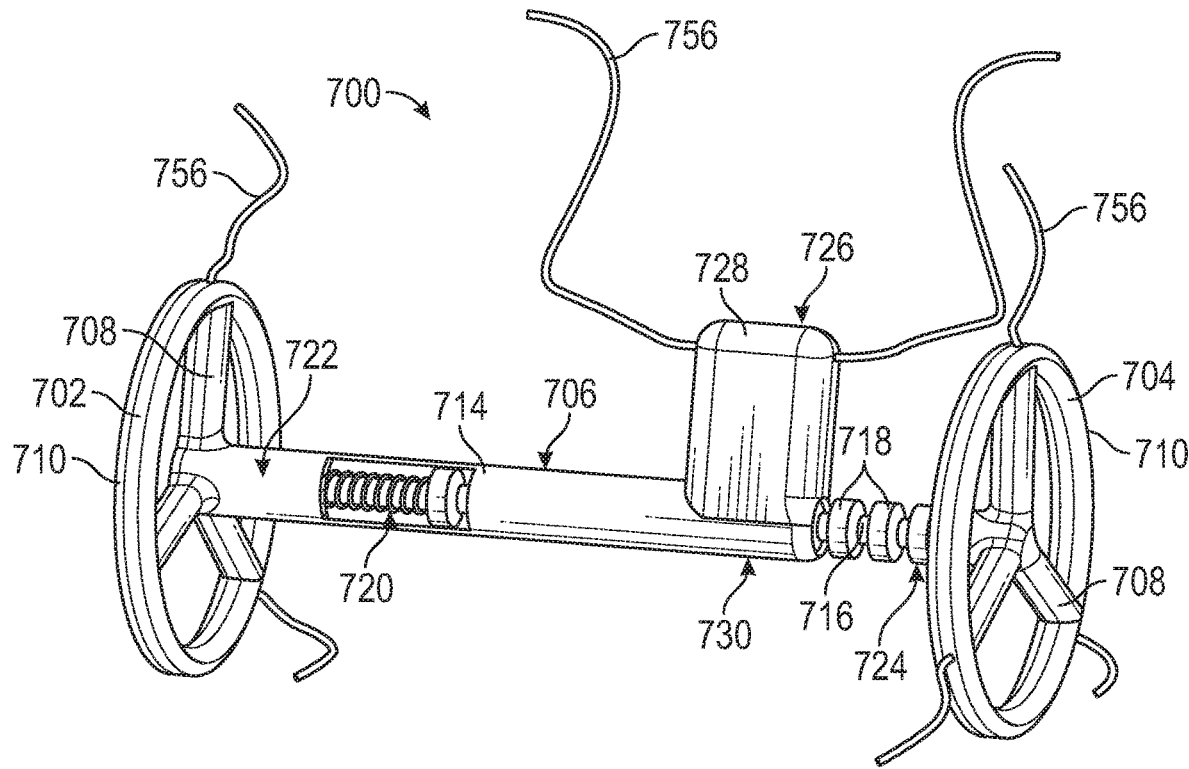
FIG. 38 is a perspective view of another embodiment of a distraction device.

FIG. 38 illustrates another embodiment of a distraction device 700 including a curved first attachment member 702, a curved second attachment member 704, and a tubular extension member 706 extending axially between the first and second attachment members. The first and second attachment members 702, 704 can include respective ring or collar portions 710 and 712, and a plurality of support members 708 extending radially between the portions 710, 712 and the extension member 706. In the illustrated embodiment, each of the attachment members 702, 704 includes three support members 708, although the attachment members may include more or fewer support members depending upon the particular application. In certain embodiments, the first and second attachment members 702 and 704 can comprise a resilient biocompatible material such as silicone, and can include an embedded suture-retention structure or layer (e.g., metal or polyester mesh) to facilitate suturing the attachment members within the lumen of the bowel, as described above.

The extension member 706 can comprise a first tubular member or portion 714 and a second cylindrical or tubular member or portion 716. The second member 716 can be disposed coaxially within and movable relative to the first member 714 in a telescoping manner between a retracted position (corresponding to the initial length of the device at implantation) and an extended position (corresponding to an extended length). The second member 716 can include a plurality of engagement members 718 (e.g., configured as collars, rings, teeth, or flanges) spaced apart from each other along a length of the member 716. The first member 714 can include a spring 720 disposed within its lumen. When the second member 716 is in the retracted position, the second member can compress the spring 720. In the illustrated embodiment, the first attachment member 702 is coupled to a first end portion 722 of first member 714, and the second attachment member 704 is coupled to a second end portion 724 of the second member 716 opposite the first attachment member 702.

The device 700 can include an actuator assembly 726 disposed within a housing 728 coupled to a second end portion 730 of the first tubular member 714. With reference to FIGS. 39A-39C, the actuator assembly 726 can comprise a first actuator member 732 and a second actuator member 734. The first actuator member 732 can be configured as a cylindrical body including a magnet portion 736 and a foot portion 738. The second actuator member 734 can be configured similarly with a magnet portion 740 and a foot portion 742. In the illustrated embodiment, the south pole S of the magnet portion 736 of the first actuator member 732 can be aligned with the north pole N of the magnet portion 740 of the second actuator member 734 and vice versa. Thus, magnetic interaction between the magnet portions 736 and 740 of the actuator members 732 and 734 can keep the actuator members in the initial, default position illustrated in FIG. 39A. The first and second actuator members 732 and 734 can extend through an opening or groove 750 defined in the first tubular member 714. In the illustrated configuration, the first actuator member 732 contacts a stop member 752 located at the top of the housing 728, and configured to prevent axial movement of the actuator member 732 toward the top of the housing.

In FIG. 39A, a protrusion 744 on the foot portion 742 of the second actuator member 734 can be disposed between two engagement members 718A and 718B of the second member 716, and can prevent axial movement of the second member 716 relative to the first tubular member 714. A protrusion 746 on the foot portion 738 of the first actuator member 732 can be disposed on an apex of an engagement member 718C.

When implanted in the lumen of an organ such as the bowel, the attachment members 702 and 704 can be sutured to the bowel wall, for example, with sutures 756. In certain embodiments, the housing 728 can also be sutured to the bowel such that the top of the housing 728 is oriented toward the outside of the body (e.g., toward the anterior abdominal wall).

After implantation of the device, the axial distance between the first and second attachment members 702 and 704 can be increased by applying a magnetic field from an external control device configured as a magnet 748 shown in FIG. 39B. In the illustrated embodiment, the magnet 748 includes a north pole N and a south pole S. When the south pole S is brought adjacent the actuator assembly 726 (e.g., from outside the body, perpendicular to the longitudinal axis of the distraction device), the associated magnetic field can overcome the magnetic interaction between the magnet portions 736 and 740 of the first and second actuator members 732 and 734. More specifically, the south pole S of the control magnet 748 can repel the upwardly oriented south pole S of the magnet portion 736, causing the first actuator member 732 to move downwardly toward the second tubular member 716 and behind (e.g., to the left in FIG. 38B) the engagement member 718C. Meanwhile, the south pole S of the control magnet 748 can attract the north pole N of the magnet portion 740, causing the second actuator member 734 to move upwardly toward the control magnet 748 and contact a stop member 754 inside the housing. This can allow the engagement member 718B to advance past the foot portion 742 in the direction of arrow 758. The protrusion 746 can then contact the next engagement member 718D, preventing further axial motion of the second member 716. When the influence of the control magnet 748 is removed, the first and second actuator members 732 and 734 can return to the initial, equilibrium position shown in FIG. 39C, with the second member 716 having advanced from the tubular member 714 by a distance equal to the spacing between the engagement members 718B and 718C, and the with protrusion 746 resting atop the engagement member 718D. This process can be repeated until a selected amount of bowel distraction has been achieved.

As noted above with respect to the preceding embodiments, any of the components of the device 700 can comprise biodegradable materials such that the device can naturally break down over a selected period of time, and can pass naturally from the bowel after the distraction procedure without requiring a second surgery to retrieve the device.

Additionally, although the description of the devices above and the examples below are primarily with respect to bowel lengthening, the distraction device embodiments described herein may also be used to lengthen other tubular organs, such as the esophagus. For example, the distraction devices described herein may be employed to treat patients with esophageal atresia and short esophagus, and/or patients where the esophagus has been shortened by resection. Lengthening of, and tissue creation in, the esophagus by distraction in patients with these conditions can restore the proper functioning of the esophagus. In addition, the various tubular members, attachment members, etc., of the distraction devices described herein may be configured as separable halves that may be assembled around the exterior of a tubular organ, such as the large or small intestine. This can allow the distraction devices to be used to lengthen the organ without requiring resecting, anastomosing, or perforating of the organ.

Example 1

In a representative example procedure, a distraction device configured as any of the embodiments described herein is implanted in one or more test animals, such as pigs weighing between 20 to 25 kg. Anesthesia induction can be performed with intravenous injection of propofol (3 mg/kg) and pancuronium (0.2 mg/kg), then maintained with 2% isoflurane. The experimental animal can be sacrificed by injection of a lethal dose of potassium chloride while under general anesthesia.

A representative procedure can include the following steps, which may occur in any suitable order: shave the anterior abdominal wall hair of the patient (e.g., an animal such as a pig), prep, and drape the abdomen; make a small incision for the first trocar placement and insert the laparoscopic camera; make additional small incisions for placement of other trocars under direct vision from the laparoscopic camera; identify the site for anastomosis and divide the small bowel at this site to simulate the problem; introduce the distraction device through one of the trocar incisions into the abdominal cavity; insert the distraction device in the distal intestinal loop and fix it to the intestinal wall on both ends with pledgeted sutures with the distracting end away from the anastomosis site; re-anastomose the two bowel segments; fix the intestinal loop containing the anastomosis site and the implanted device to the interior side of the anterior abdominal wall; align and connect the magnetic remote control, from outside the body, to the device and start distraction; distract the full length of the device in increments (e.g., 1-10 mm/day, for example 5 mm/day); and record the distraction process using the laparoscopic camera. Simultaneous distraction with two devices in two different anastomosis sites may be performed. Once the distraction procedure is complete, the prototypes are retrieved and the small intestine re-anastomosed.

Example 2

In another representative example, a subject is selected who requires distraction of the bowel. The introduction of the distraction device can be performed using appropriate anesthesia and pain control. The distraction device is introduced between two resected ends of the bowel and the ends of the bowel are secured to the ends of the device. The lengthening process, through the device distraction, can start 24 hours after surgery for 5 mm/day. The subject can be sedated to conduct the distraction procedure and provided with pain management medications. The subject can have normal access to food and water through the lengthening phase.

When the procedure is performed on test animals, the subjects can have a second surgery, using the same protocol as the first surgery, to harvest the newly formed bowel tissue for histological examination and to retrieve the devices.

The device implantation surgery can proceed in the following manner: induction of general anesthesia; shave the anterior abdominal wall hair, prep, and drape the abdomen; make an incision for the first trocar placement and insert the laparoscopic camera; after initial abdominal cavity inspection, make three small incisions for placement of other trocars under direct vision from the laparoscopic camera; identify the site for anastomosis and divide the small bowel at this site to simulate the problem; introduce the distraction device through one of the trocar incisions into the abdominal cavity; insert the distraction device in the distal intestinal loop and suture it to the intestinal wall on both ends with pledgeted sutures with the distracting end away from the anastomosis site; re-anastomose the two bowel segments; fix the intestinal loop containing the anastomosis site and the implanted device to the interior side of the anterior abdominal wall. In test animals, another bowel segment can be chosen as a control and the segment marked with a permanent marker for the same length as a non-distracted device. The control segment is fixed to the interior side of the anterior abdominal wall. Surgical instruments can then be removed from the abdominal cavity, and the trocar sites can be closed.

A representative distraction or bowel lengthening procedure can begin about 24 hours after the initial device implantation surgery. The subject can have the implanted device distracted for 5 mm daily until full distraction of the device is achieved. The distraction can be done remotely using a magnetic remote control (such as the control 300) that connects to the magnets in the implanted device from outside the body. After the remote control is coupled (e.g., magnetically) to the device and aligned in the correct direction, it can be moved perpendicularly and/or longitudinally relative to the implanted device to achieve distraction of 5 mm during each distraction event. The distance of distraction can be controlled by the distraction device design. Because the distraction is done remotely, there may not be pain related to the process other than some visceral pain that may be induced from the device movement in the intestine.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. An implantable distraction device, comprising:
a tubular member oriented along a longitudinal axis of the distraction device and defining a lumen;

a curved first attachment member coupled to a first end portion of the tubular member and configured to be sutured within a body lumen;
a curved second attachment member coupled to the tubular member and configured to be sutured within a body lumen, the second attachment member being spaced apart from the first attachment member along the tubular member;
an annular actuator member movably disposed on the tubular member; and
a plurality of magnets coupled to the actuator member and circumferentially arrayed around the actuator member;
wherein the second attachment member is axially movable relative to the first attachment member between a first position and a second position to vary an axial distance between the first and second attachment members; and
wherein the plurality of magnets are configured such that motion of a magnetic field relative to the distraction device causes corresponding motion of the actuator member, and corresponding motion of the second attachment member relative to the first attachment member.

2. The implantable distraction device of claim 1, wherein:
the tubular member comprises a channel extending along the length of the tubular member; and
the actuator member comprises an engagement member configured to engage the channel such that the actuator member is movable along a path defined by the channel.

3. The implantable distraction device of claim 2, wherein the channel comprises a plurality of axially-extending channel portions interconnected by circumferentially-extending channel portions.

4. The implantable distraction device of claim 2, wherein the channel extends helically along the length of the tubular member.

5. The implantable distraction device of claim 4, wherein:
the channel comprises a plurality of first channel portions extending along the tubular member at an angle to the longitudinal axis of the distraction device; and
the first channel portions are interconnected by second channel portions extending axially along the tubular member.

6. The implantable distraction device of claim 1, wherein:
the actuator member is positioned between the first attachment member and the second attachment member; and
the actuator member is configured to engage the second attachment member such that axial motion of the actuator member along the tubular member causes corresponding axial motion of the second attachment member toward the second position.

7. The implantable distraction device of claim 1, wherein the first attachment member comprises a flexible, annular suture retention member configured to be sutured to a body lumen.

8. A system, comprising:
an implantable distraction device, the distraction device including a tubular member oriented along a longitudinal axis of the distraction device and defining a lumen, a curved first attachment member coupled to a first end portion of the tubular member and configured to be sutured within a body lumen, a curved second attachment member coupled to the tubular member and configured to be sutured within a body lumen, the second attachment member being spaced apart from the first attachment member along the tubular member, an annular actuator member movably disposed on the tubular member, a plurality of magnets coupled to the actuator member and circumferentially arrayed around the actuator member, the second attachment member being axially movable relative to the first attachment member between a first position and a second position to vary an axial distance between the first and second attachment members, the plurality of magnets being configured such that motion of a magnetic field relative to the distraction device causes corresponding motion of the actuator member, and corresponding motion of the second attachment member relative to the first attachment member; and
a control device including a plurality of magnets configured to magnetically couple with the plurality of magnets of the distraction device such that motion of the control device in a direction along a longitudinal axis of the distraction device, or motion of the control device perpendicular to the longitudinal axis of the distraction device, causes corresponding motion of the actuator member and the second attachment member of the distraction device relative to the first attachment member.

9. The system of claim 8, wherein the control device comprises a housing, and the plurality of magnets of the control device are disposed on a surface of the housing.

10. A method, comprising:
implanting a distraction device in a lumen of a patient's body, the distraction device including a tubular member oriented along a longitudinal axis of the distraction device and defining a distraction device lumen, a curved first attachment member coupled to a first end portion of the tubular member and configured to be sutured within the body lumen, a curved second attachment member coupled to the tubular member and configured to be sutured within the body lumen, the second attachment member being spaced apart from the first attachment member along the tubular member, an annular actuator member movably disposed on the tubular member, and a plurality of magnets coupled to the actuator member and circumferentially arrayed around the actuator member, the second attachment member being axially movable relative to the first attachment member or between a first position and a second position to vary an axial distance between the first and second attachment members, and the plurality of magnets being configured such that motion of a magnetic field relative to the distraction device causes corresponding motion of the actuator member, and corresponding motion of the second attachment member relative to the first attachment member;
attaching the first and second attachment members to the lumen of the patient's body;
applying a magnetic field to the plurality of magnets of the distraction device from outside the lumen of the patient's body such that the actuator member and the second attachment member move longitudinally relative to the first attachment member to apply tension to tissue of the body lumen between the first and second attachment members.

11. The method of claim 10, wherein attaching the first and second attachment members further comprises suturing the first and second attachment members within the lumen of the patient's body.

12. The method of claim 10, wherein:
the magnetic field is associated with a control device including a plurality of magnets configured to magnetically couple with the plurality of magnets of the actuator member; and
moving the magnetic field further comprises moving the control device axially along the tubular member.

13. The method of claim 10, wherein the method is a distraction enterogenesis method and the lumen of the patient's body is an intestine.

14. The method of claim 13, wherein the intestine is a small intestine.

15. The implantable distraction device of claim 7, wherein the flexible suture retention member is received in a channel defined around a circumference of the first attachment member.

16. The implantable distraction device of claim 7, wherein the flexible suture retention member comprises a braided layer or mesh.

17. The implantable distraction device of claim 16, wherein the braided layer or mesh is encapsulated in a polymeric layer.

18. The implantable distraction device of claim 16, wherein the braided layer or mesh comprises a plurality of polymeric or metal filaments.

19. The implantable distraction device of claim 1, wherein the first attachment member is integrally formed with the tubular member.

20. The implantable distraction device of claim 1, wherein the tubular member defines a plurality of non-intersecting channels that are angularly spaced apart from each other around a circumference of the tubular member.

21. The implantable distraction device of claim 20, wherein the actuator member comprises a plurality of engagement members, each of the engagement members being positioned about a circumference of an inner surface of the actuator member to engage a respective channel of the tubular member.

22. The implantable distraction device of claim 21, wherein the engagement members comprise rods, balls, or spheres.

* * * * *